(12) United States Patent
Hou et al.

(10) Patent No.: US 11,834,516 B2
(45) Date of Patent: Dec. 5, 2023

(54) TUMOR-SPECIFIC POLYPEPTIDE AND USE THEREOF

(71) Applicant: GENOIMMUNE THERAPEUTICS CO., LTD., Wuhan (CN)

(72) Inventors: Yong Hou, Shenzhen (CN); Shuntao Luo, Shenzhen (CN); Ting An, Shenzhen (CN); Xiumei Lin, Shenzhen (CN); Bo Li, Shenzhen (CN); Guanglei Li, Shenzhen (CN)

(73) Assignee: GENOIMMUNE THERAPEUTICS CO., LTD., Hubei (CN)

( * ) Notice: Subject to any disclaimer, the term of this patent is extended or adjusted under 35 U.S.C. 154(b) by 0 days.

(21) Appl. No.: 17/491,219

(22) Filed: Sep. 30, 2021

(65) Prior Publication Data

US 2022/0033438 A1  Feb. 3, 2022

Related U.S. Application Data

(63) Continuation of application No. 16/326,659, filed as application No. PCT/CN2016/096020 on Aug. 19, 2016, now Pat. No. 11,161,874.

(51) Int. Cl.
*C07K 7/06* (2006.01)
*A61P 35/00* (2006.01)
*C07K 14/74* (2006.01)
*G01N 33/68* (2006.01)
*A61K 39/00* (2006.01)

(52) U.S. Cl.
CPC .............. *C07K 7/06* (2013.01); *A61P 35/00* (2018.01); *C07K 14/70539* (2013.01); *G01N 33/6848* (2013.01); *A61K 39/00* (2013.01)

(58) Field of Classification Search
CPC ..... C07K 7/06; C07K 14/70539; A61P 35/00; G01N 33/6848; A61K 39/00
See application file for complete search history.

(56) References Cited

U.S. PATENT DOCUMENTS

| 2002/0076412 A1 | 6/2002 | Steinman et al. |
| 2008/0166729 A1 | 7/2008 | Kim et al. |
| 2013/0143318 A1 | 6/2013 | Rothblum |

FOREIGN PATENT DOCUMENTS

WO    WO 01/83524 A2    11/2001

OTHER PUBLICATIONS

Lili Qin, Novel pipeline of high-frequency neoantigens heathy donor-based validation in breast cancer , pp. 1-36, BioRxiv, published 2019.*
Liu, "Study on Cloning, Expression and Localization of One PRA43 related gene (BmRPA43_N) in Slikworm, *Bombyx mori*", Basic Sciences, China Master's Theses Full-Text Database), Jun. 2011.
Ota et al., "Accession No. Q3B726.1 RecName: Full=DNA-directed RNA polymerase I submit RPA43; AltName: Full=Twist neighbour", UniProtKB / Swiss-Prot Database, Jul. 2016.
Rothblum et al., "Selective Inhibition of rDNA Transcription by a Small-Molecule Peptide That Targets the Interface between RNA Polymerase I and Rrn3", Molecular Cancer Research, Nov. 2014, 12(11): 1586-1596.
Yang et al., "Exploring a New Twist on Tumor Metastasis", Cancer Research, May 2006, 66(9): 4549-4552.
UniProtKB—Q3B726 (RPA43_Human), Dn DNA-Directed RNA-directed RNA polymerase I subunit RPA43, protein database accessed on Jan. 25, 2021.
The online medical dictionary, Definition of Derivative, pp. 1-2, accessed on Jul. 7, 2005.

* cited by examiner

*Primary Examiner* — Julie Ha
*Assistant Examiner* — Erinne R Dabkowski
(74) *Attorney, Agent, or Firm* — James S. Keddie; Bozicevic, Field & Francis LLP

(57) ABSTRACT

The present invention relates to a novel tumor-specific polypeptide and use thereof. In particular, the present invention relates to a tumor-specific polypeptide having high affinity for HLA-A0201 and having cytotoxic T lymphocyte inducing ability, and its use for diagnosing, preventing and treating diseases (especially cancer) associated with high expression of the TWISTNB gene or mutation(s) in the TWISTNB gene.

6 Claims, 6 Drawing Sheets

Specification includes a Sequence Listing.

Blank    Wild-type polypeptide    KLMGIVYKV polypeptide

KLMGIVYKV polypeptide    Control

TUMOR-SPECIFIC POLYPEPTIDE AND USE THEREOF

TECHNICAL FIELD

The present invention relates to the field of biomedicine, in particular, the present invention relates to a polypeptide and use thereof, and more particularly to a polypeptide and its use in the preparation of a kit, medicament, or vaccine, and to a pharmaceutical composition, DC cell, targeting immune cell population, vaccine, antibody, and to a method of preparing an antibody, a method of treatment, a diagnostic method, and a diagnostic system.

BACKGROUND

Cancer is a disease caused by uncontrolled cell proliferation due to genetic mutations in cells. So far, cancer has become a major threat to human health and it is one of the leading causes of human death. According to World Cancer Report 2014 published by World Health Organization (WHO), cancer patients and deaths are rapidly increasing all over the world in 2012, and nearly half of new cancer cases occur in Asia, wherein most of which arise in China and China ranks first in terms of new cancer cases (see World Health Organization. Globocan 2012: Estimated cancer incidence, mortality and prevalence worldwide in 2012). According to the data of China Cancer Registry Annual Report 2012, there are about 3.5 million new cancer cases in China each year, and about 2.5 million people die from cancer (Bernard W. Stewart C P W. World Cancer Report 2014). Therefore, it is of great clinical value to find a highly effective and specific method for cancer treatment.

Traditional cancer treatment methods mainly include surgery, radiotherapy and chemotherapy; however, these methods have great limitations. Due to the proximal invasion or distant metastasis of cancer cells, the recurrence of tumor metastasis after surgical resection is high; radiotherapy and chemotherapy can cause serious damage to the body's own normal cells, especially those of the hematopoietic system and immune system, thus, it is difficult for patients with cancer metastasis to achieve good long-term efficacy (Ha Xiaoqin, Zhang Shangdi, Yang Zhihua, Zhang Jun. New technology for tumor biotherapy—targeted gene therapy. Medical & Pharmaceutical Journal of Chinese People's Liberation Army. 2014; 26: 24-7.).

With the in-depth study of the molecular mechanisms of cancer and the further development of biotechnology, targeted therapy and immunotherapy play an increasingly important role in the comprehensive treatment of cancer. Targeted therapies mainly include monoclonal antibodies (sometimes classified as passive immunotherapy) and small molecule targeted drugs, while immunotherapy mainly includes cytokine therapy, immune checkpoint blockade, adoptive cell reinfusion, and tumor vaccine (Mellman I, Coukos G, Dranoff G. Cancer immunotherapy comes of age. Nature 2011; 480: 480-9; Chen D S, Mellman I. Oncology meets immunology: the cancer-immunity cycle. Immunity 2013; 39: 1-10). Immunotherapies control and kill tumor cells by regulating the immune system of the body and enhancing the anti-tumor immunity of the tumor microenvironment, have the advantages of high efficiency, high specificity and good tolerance, and have broad prospects in tumor treatment (Chen D S, Mellman I. Oncology meets immunology: the cancer-immunity cycle. Immunity 2013; 39: 1-10; Currie G A. Eighty years of immunotherapy: a review of immunological methods used for the treatment of human cancer. British journal of cancer 1972; 26: 141-53.).

Tumor vaccines for immunotherapy mainly include tumor cell vaccine, dendritic cell vaccine, protein and peptide vaccine, nucleic acid vaccine, genetic engineering vaccine and anti-idiotype tumor vaccine (Li Tingting, Li Hui, Wang Xicai. The progress of tumor vaccine in oncotherapy. Journal of Modern Oncology. 2013; 21:2351-3). The main mechanism by which these vaccines can kill tumors is to enable patients to produce immune responses against tumor-specific antigens, including antigen-antibody reactions and cytotoxic T-lymphocyte (CTL)-specific killing, among which CTL-specific killing plays a key role in the immune responses.

A tumor-specific polypeptide is a tumor-specific antigen that primarily induces CTL and causes CTL-specific killing of target cells. Tumor-specific polypeptides include tumor's mutated polypeptides as well as tumor-specifically highly expressed polypeptides. The tumor's mutated polypeptides are specific targets of tumor immunotherapy because they are only present in the tumor tissues of the patient, and have the characteristics of good safety and fewer side effects. Immunotherapy for targeting tumor's mutated polypeptides, represented by adoptive transfer of polypeptide-specific DC-CTL and TIL, has good therapeutic effects (Tran E, Turcotte S, Gros A, et al. Cancer immunotherapy based on mutation-specific CD4+ T cells in a patient with epithelial cancer. Science. 2014. 344(6184): 641-5; Cobbold M, De La Pena H, Norris A, et al. MHC class I-associated phosphopeptides are the targets of memory-like immunity in leukemia. Sci Transl Med. 2013. 5(203): 203ra125).

Tumor-specific polypeptides can be recognized by CTL or tumor-infiltrating lymphocytes (TIL) and require antigen presentation function of human leukocyte antigen (HLA). Different polypeptides differ in their ability to bind to a specific subtype of HLAs. In tumor patients with specific HLA subtypes, HLA subtypes determine that only certain mutated polypeptides are capable of binding to their HLA and are presented by their HLA to CTL or TIL cells. HLAs can be primarily classified into type I HLAs and type II HLAs. Type I HLAs can be mainly divided into three subtypes of HLA-A, HLA-B and HLA-C; wherein, for each subtype, according to its sequence, it can be divided into various subtypes. HLA-A0201 is a member of the HLA-A subtypes and accounts for a high proportion of approximately 13% in the Chinese population.

The TWISTNB (Twist neighbor) gene encodes a protein of 338 amino acids in length and 37,432 Daltons in molecular weight. This protein is called Twist neighbor protein, or DNA-directed RNA polymerase I subunit RPA43, GeneBank accession number is Q3B726, and its amino acid sequence is shown in SEQ ID NO: 1. The Twist neighbor protein functions in vivo mainly as a DNA-dependent RNA polymerase. As a component of RNA polymerase I, it catalyzes a transcription reaction from DNA to RNA and is lowly expressed in normal tissues of adults. The high expression of mutated TWISTNB gene can be found in tumor tissues. To date, TWISTNB gene-related peptides for use immunotherapy of tumors have not been reported in China and other countries. Therefore, TWISTNB gene-related tumor-specific peptides are of great significance for detection, early prevention, and immunotherapy in patients with tumor.

SUMMARY OF THE INVENTION

The present invention relates to a novel tumor-specific polypeptide and uses thereof. Specifically, the present inventors have unexpectedly found that the polypeptide of the present invention has high affinity for an HLA antigen, particularly an HLA-A0201 antigen, and can be used as a tumor-specific antigen of a tumor with high expression of the TWISTNB gene or mutation(s) in the TWISTNB gene, and efficiently induce CTL for the prevention or treatment of diseases associated with high expression of the TWISTNB gene or mutation(s) in the TWISTNB gene, especially cancer.

Accordingly, the present application includes the following embodiments and any combination thereof.

1. A polypeptide or a derivative thereof selected from the group consisting of
   a) a polypeptide comprising or consisting of the amino acid sequence KLMGIVYKV (SEQ ID NO: 2); or
   b) a polypeptide having an amino acid sequence at least 70%, at least 75%, at least 80%, at least 85%, at least 90%, at least 95%, at least 99% identical to SEQ ID NO: 2, wherein said polypeptide has the ability of inducing cytotoxic T lymphocyte cells; or
   c) a polypeptide having an amino acid sequence comprising at least one or several amino acid substitutions, deletions and/or additions compared to SEQ ID NO: 2, wherein said polypeptide has the ability of inducing cytotoxic T lymphocyte cells; or
   d) a polypeptide derivative which is a derivative of any of a)-c), wherein the polypeptide derivative has the ability of inducing cytotoxic T lymphocyte cells.
2. The polypeptide or derivative thereof according to item 1, wherein the second amino acid from the N-terminus of the amino acid sequence of the polypeptide is substituted with leucine or methionine, and/or the amino acid at the C-terminus is substituted with valine or leucine.
3. The polypeptide or derivative thereof according to item 1 or 2, comprising a TWISTNB protein fragment having an amino acid sequence with a substitution and addition of at least one or several amino acids compared to SEQ ID NO: 2, or a TWISTNB protein fragment comprising the polypeptide of SEQ ID NO: 2.
4. The polypeptide or derivative thereof according to any one of items 1 to 3, which comprises or consists of the following amino acid sequence:

```
                         (SEQ ID NO: 2)
    KLMGIVYKV;

(SEQ ID NO: 3)
    KMMGIVYKV;

(SEQ ID NO: 4)
    KLMGIVYKL;

(SEQ ID NO: 5)
    KMMGIVYKL.
    ```

5. A polynucleotide encoding the polypeptide of any one of items 1 to 4.
6. A nucleic acid construct comprising the polynucleotide of item 5, and one or more regulatory sequences operably linked thereto that direct expression of the polypeptide in a host cell.
7. A vector comprising the polynucleotide of item 5.
8. A host cell which is transformed or transfected with the nucleic acid construct according to item 6 or the vector according to claim 7.
9. A conjugate comprising the polypeptide or derivative thereof according to any one of items 1 to 4, or the polynucleotide according to item 5, or the nucleic acid construct of item 6, or the vector according to item 7, or the host cell according to item 8.
10. A pharmaceutical composition comprising the polypeptide or derivative thereof according to any one of items 1 to 4, or the polynucleotide according to item 5, or the nucleic acid construct of item 6, or the vector according to item 7, or the host cell according to item 8; optionally comprising an adjuvant and/or a pharmaceutically acceptable carrier.
11. An in vitro method of producing antigen presenting cells, the method comprising the steps of:
    (a) contacting an antigen presenting cell with the polypeptide or derivative thereof according to any one of items 1 to 4, or
    (b) introducing the polynucleotide according to item 5, or the nucleic acid construct of item 6, or the vector according to item 7 into an antigen presenting cell.
12. An antigen presenting cell which presents the polypeptide or derivative thereof according to any one of items 1 to 4 on the cell surface.
13. The antigen presenting cell according to item 12, which is produced by the method of item 11.
14. A targeting immune cell population obtained or obtainable by co-culturing the antigen presenting cell according to item 12 or 13 with a lymphocyte.
15. A method of producing an immune effector cell, comprising: a step of contacting the polypeptide or derivative thereof according to any one of items 1 to 4 with an immune cell; preferably, the immune cell is a T lymphocyte, preferably a CD8+ T lymphocyte.
16. The method according to item 15, wherein the immune cell is contacted with the polypeptide or derivative thereof according to any one of items 1 to 4 through an antigen presenting cell.
17. An immune effector cell produced by the method of item 15 or 16.
18. A vaccine or a pharmaceutical composition, comprising the polypeptide or derivative thereof according to any one of items 1 to 4, or the polynucleotide according to item 5, or the nucleic acid construct of item 6, or the vector according to item 7, or the host cell according to item 8, or the antigen presenting cell according to any one of items 12 to 13, or the targeting immune cell population according to item 14, or the immune effector cell according to item 17.
19. The vaccine according to item 18, further comprising an adjuvant.
20. The vaccine according to any one of items 18 to 19, which is formulated for administration to a subject having an HLA antigen of the HLA-A2 subtype, preferably the HLA-A0201 subtype.
21. An antibody, which specifically recognizes the vaccine according to any one of items 18 to 19.
22. A method of preparing an antibody, comprising:
collecting serum of an animal immunized with the vaccine according to any of claims 18-19; and
purifying the antibody of interest from the serum.
23. The polypeptide or derivative thereof according to any one of items 1 to 4, or the polynucleotide according to item 5, or the nucleic acid construct of item 6, or the vector according to item 7, or the host cell according to item 8, or the antigen presenting cell according to any one of items 12 to 13, or the targeting immune cell population according to item 14, or the immune effector cell according to item 17, or the vaccine according to any one of items 18 to 19, or the antibody according to item 21 for use in preventing or treating a disease associated with high expression of the TWISTNB gene or mutation(s) in the TWISTNB gene in a subject.

24. The polypeptide or derivative thereof, the polynucleotide, the nucleic acid construct, the vector, the host cell, the antigen presenting cell, the targeting immune cell population, the immune effector cell, the vaccine, or the antibody according to item 23, wherein the disease is cancer.

25. The polypeptide or derivative thereof, the polynucleotide, the nucleic acid construct, the vector, the host cell, the antigen presenting cell, the targeting immune cell population, the immune effector cell, the vaccine, or the antibody according to item 24, wherein the cancer includes breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumor.

26. The polypeptide or derivative thereof, the polynucleotide, the nucleic acid construct, the vector, the host cell, the antigen presenting cell, the targeting immune cell population, the immune effector cell, the vaccine, or the antibody according to any one of items 22 to 25, wherein the subject is a mammal; preferably, the subject is a human.

27. The polypeptide or derivative thereof, the polynucleotide, the nucleic acid construct, the vector, the host cell, the antigen presenting cell, the targeting immune cell population, the immune effector cell, the vaccine, or the antibody according to any one of items 23-26, wherein the subject's HLA antigen is an HLA-A2 subtype, preferably an HLA-A0201 subtype.

28. Use of the polypeptide or derivative thereof according to any one of items 1 to 4, or the polynucleotide according to item 5, or the nucleic acid construct of item 6, or the vector according to item 7, or the host cell according to item 8, or the antigen presenting cell according to any one of items 12 to 13, or the targeting immune cell population according to item 14, or the immune effector cell according to item 17, or the vaccine according to any one of items 18 to 19, or the antibody according to item 21 in the manufacture of a medicament for preventing or treating a disease associated with high expression of the TWISTNB gene or mutation(s) in the TWISTNB gene in a subject.

29. The use according to item 28, wherein the disease is cancer.

30. The use according to item 29, wherein the cancer comprises breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumors.

31. The use according to any one of items 28 to 30, wherein the subject is a mammal; preferably, the subject is a human.

32. The use according to item 31, wherein the subject's HLA antigen is an HLA-A2 subtype; preferably an HLA-A0201 subtype.

33. Use of the polypeptide or derivative thereof according to any one of items 1 to 4, or the polynucleotide according to item 5, or the nucleic acid construct of item 6, or the vector according to item 7, or the host cell according to item 8, or the antigen presenting cell according to any one of items 12 to 13, or the targeting immune cell population according to item 14, or the immune effector cell according to item 17 in the manufacture of a vaccine for preventing or treating a disease in a subject that is associated with high expression of the TWISTNB gene or mutation(s) in the TWISTNB gene.

34. The use according to item 33, wherein the disease is cancer.

35. The use according to item 34, wherein the cancer comprises breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumors.

36. The use according to any one of items 33 to 35, wherein the subject is a mammal; preferably, the subject is a human.

37. The use according to any one of items 33 to 36, wherein the subject's HLA antigen is an HLA-A2 subtype, preferably an HLA-A0201 subtype.

38. A method of preventing or treating a disease associated with high expression of the TWISTNB gene or mutation(s) in the TWISTNB gene in a subject, the method comprising administering to the subject an effective amount of the polypeptide or derivative thereof according to any one of items 1 to 4, or the polynucleotide according to item 5, or the nucleic acid construct of item 6, or the vector according to item 7, or the host cell according to item 8, or the antigen presenting cell according to any one of items 12 to 13, or the targeting immune cell population according to item 14, or the immune effector cell according to item 17, or the vaccine according to any one of items 18 to 19, or the antibody according to item 21.

39. The method according to item 38, wherein the disease is cancer.

40. The method according to item 39, wherein the cancer comprises breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumors.

41. The method according to any one of items 38 to 40, wherein the subject is a mammal; preferably, the subject is a human.

42. The method according to any one of items 38 to 41, wherein the subject's HLA antigen is an HLA-A2 subtype, preferably an HLA-A0201 subtype.

43. An in vitro method of diagnosing a disease associated with high expression of the TWISTNB gene or mutation(s) in the TWISTNB gene in a subject, comprising the steps of:

obtaining serum from the subject; and detecting the presence of the polypeptide or derivative thereof according to any one of items 1 to 4 in the serum.

44. The method according to item 43, wherein the detecting is performed by mass spectrometry.

45. The method according to item 43 or 44, wherein the disease is cancer.

46. The method according to any one of items 43 to 45, wherein the cancer comprises breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumors.

47. The method according to any one of items 43 to 46, wherein the subject is a mammal; preferably, the subject is a human.

48. The method according to any one of items 43 to 47, wherein the subject's HLA antigen is an HLA-A2 subtype, preferably an HLA-A0201 subtype.

49. Use of the polypeptide or derivative thereof according to any one of items 1 to 4, or the polynucleotide according to item 5, or the nucleic acid construct of item 6, or the vector according to item 7, or the host cell according to item 8, or the antigen presenting cell according to any one of items 12 to 13, or the targeting immune cell population according to item 14, or the immune effector cell according to item 17, or the vaccine according to any one of items 18 to 19, or the antibody according to item 21 in the manufacture of a diagnostic agent or kit for diagnosing a disease associated with high expression of the TWISTNB gene or mutation(s) in the TWISTNB gene in a subject.

50. The use according to item 49, wherein the disease is cancer.

51. The use according to item 50, wherein the cancer comprises breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumors.

52. The use according to any one of items 49 to 51, wherein the subject is a mammal; preferably, the subject is a human.

53. The use according to any one of items 49 to 52, wherein the subject's HLA antigen is an HLA-A2 subtype, preferably an HLA-A0201 subtype.

Beneficial Effects of the Present Invention

The polypeptide of the present invention, e.g., KLMGIVYKV polypeptide (SEQ ID NO: 2) and its alternative forms KMMGIVYKV (SEQ ID NO: 3), KLMGIVYKL (SEQ ID NO: 4), KMMGIVYKL (SEQ ID NO: 5), has strong immunogenicity and the ability to activate specific T immunity.

The polypeptide of the present invention is derived from tumor's mutated polypeptide, is absent in a human in which the mutation has not occurred, and is present only in tumor tissue of a patient in which the mutation has occurred, whereas normal tissue does not contain the mutation. Because it exists only in the patient's tumor tissue and not the normal tissue, its specificity is high and the specificity of immune response induced by it is also high. It can be prepared as a peptide vaccine, which is safer, has less side effects, and rarely causes serious immune response in comparison with other tumor polypeptide vaccines, and because its structure is simple and it is easy to synthesize it, it can be developed as a vaccine to induce an immune response against tumors.

The above-mentioned polypeptide can be used as a target or vaccine for use in biological therapy of a tumor which expresses both HLA-A0201 and the mutated polypeptide. Though the manners such as polypeptide+adjuvant, or polypeptide-loaded DC vaccine, or polypeptide-specific DC-CTL, it can be used to induce immune response, specifically kill tumor cells, prevent and treat diseases (e.g., cancer) associated with high expression or mutation of TWISTNB gene, including the types of cancer which express the above polypeptide sequence, such as lung cancer, melanoma, breast cancer, nasopharyngeal cancer, liver cancer, gastric cancer, esophageal cancer, colorectal cancer, pancreatic cancer, skin cancer, prostate cancer, cervical cancer, leukemia and brain tumors. The polypeptide vaccine of the present invention is capable of significantly inhibiting tumor growth and prolonging the survival of the subject.

Moreover, since the mutation is only found in cancer tissues, and the free polypeptide present in the serum can be detected by mass spectrometry, the mutation can be used in the diagnosis of cancer as a tumor marker.

Furthermore, the polynucleotide, the nucleic acid construct, the vector, the host cell, the antigen presenting cell, the targeting immune cell population or the immune effector cell of the present invention can also be prepared as a vaccine or a pharmaceutical composition for preventing and treating the above diseases associated with high expression of the TWISTNB gene or mutation(s) in the TWISTNB gene.

Meanwhile, the polynucleotide, the nucleic acid construct, the vector, the host cell, the antigen presenting cell, the targeting immune cell population or the immune effector cell, the vaccine or the antibody of the present invention can be used in the manufacture of a diagnostic agent or kit for diagnosis of a disease associated with high expression of the TWISTNB gene or mutation(s) in the TWISTNB gene.

In the context of the present invention, "mutated polypeptide" or "polypeptide of the present invention" means a polypeptide that is mutated relative to a wild-type polypeptide (i.e., the peptide fragment as shown by amino acids 130-138 in the unmutated Twist neighbor protein, the sequence of which is KLMGIVNKV (SEQ ID NO: 6). In a specific embodiment, particularly an example of the present invention, "mutated polypeptide" or "polypeptide of the present invention" specifically refers to the polypeptide as set forth in SEQ ID NOs: 2-5, respectively, particularly the polypeptide as set forth in SEQ ID NO: 2.

The objects and features of the present invention will become more apparent from the detailed description of the present invention in combination with the description of the drawings and the examples. However, it will be understood by those skilled in the art that the above and following description are preferred embodiments of the present invention, and are not intended to limit the present invention.

DESCRIPTION OF THE DRAWINGS

FIG. 4, panel A shows the inhibitory effect on tumor growth after treatment with adjuvant, adjuvant+wild type polypeptide, and adjuvant+mutated polypeptides. From top to bottom: SEQ ID NOS 2, 3, 4, and 5. FIG. 4, panel B shows the survival rate of mice after treatment with adjuvant, adjuvant+wild type polypeptide, and adjuvant+mutated polypeptides. From top to bottom: SEQ ID NOS 2, 3, 4, and 5.

FIG. 5, panel A shows the inhibitory effect on tumor growth after treatment with DC-loaded with wild-type (KLMGIVNKV (SEQ ID NO: 6)) polypeptide, and DC-loaded with mutated polypeptides (SEQ ID NO: 2-5). From top to bottom: SEQ ID NOS 2, 3, 4, and 5. FIG. 5, panel B shows the survival rate of mice after treatment with DC-loaded with wild-type (KLMGIVNKV) polypeptide (SEQ ID NO: 6), and DC-loaded with mutated polypeptides (SEQ ID NO: 2-5). From top to bottom: SEQ ID NOS 2, 3, 4, and 5.

FIG. 6, panel A shows the inhibitory effect of the treatment on tumor growth after transfection of DC with a lentiviral vector carrying the wild type (SEQ ID NO: 6) or mutated polypeptide (SEQ ID NO: 2-5) sequences. From top to bottom: SEQ ID NOS 2, 3, 4, and 5. FIG. 6, panel B shows the survival rate of mice treated after transfection of DCs with lentiviral vectors carrying wild-type or mutated polypeptide sequences. From top to bottom: SEQ ID NOS 2, 3, 4, and 5.

FIG. 7, panel A shows the inhibitory effect on tumor growth after treatment with DC-loaded with wild-type polypeptide (SEQ ID NO: 6)+CTL, and DC-loaded with mutated polypeptides (SEQ ID NO: 2-5)+CTL. From top to bottom: SEQ ID NOS 2, 3, 4, and 5. FIG. 7, panel B shows the survival rate of mice after treatment with DC-loaded with wild-type polypeptide+CTL, and DC-loaded with mutated polypeptides+CTL. From top to bottom: SEQ ID NOS 2, 3, 4, and 5.

DETAILED DESCRIPTION OF THE PRESENT INVENTION

Definition

Figure 1:
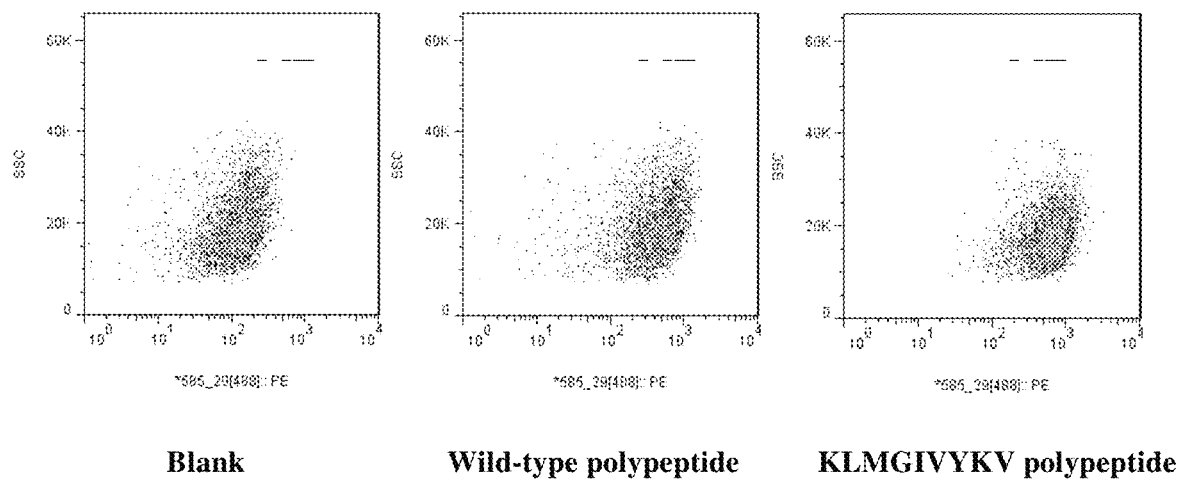
FIG. 1 shows the affinity of polypeptides for T2 cells as determined by flow cytometry. The sequence shown in FIG. 1 is SEQ ID NO: 2.

Unless otherwise defined, the terms "a" or "an" and "the" as used herein refer to at least one.

Unless otherwise defined, all technical and scientific terms used in the specification have the same meaning as commonly understood by those skilled in the art.

The term "polypeptide" as used herein refers to a linear polymer of two or more amino acids joined by peptide bonds.

The term "polynucleotide" as used herein refers to a linear multimer of more than 10 nucleotides joined by 3',5'-phosphodiester bonds.

The term "gene" as used herein refers to a genetic unit that occupies a particular locus on a chromosome.

The parameter "identity" describes the correlation between two amino acid sequences or between two nucleotide sequences. The degree of sequence identity between two amino acid sequences can be determined using software packages or programs well known to those skilled in the art, such as the EMBOSS software package (EMBOSS: The European Molecular Biology Open Software Suite, Rice et al, 2000; http://emboss.org) or BLAST sequence alignment tool (http://blast.ncbi.nlm.nih.gov/Blast.cgi).

The term "fragment" means a polypeptide having one or more (several) amino acids deleted from the amino and/or carboxyl terminus of the polypeptide.

The term "cytotoxic T lymphocyte inducing ability" as used herein refers to the ability to induce cytotoxic T lymphocytes, for example, to stimulate CD8+ T cell expansion and activate CD8+ T cell immune response.

The term "variant" means a polypeptide comprising amino acid changes at one or more (several) positions, i.e., substitution, insertion and/or deletion of one or more (several) amino acid residues, and having the activity of the parent or wild type polypeptide. "Substitution" means replacing an amino acid occupying a position with a different amino acid; "deletion" means removing an amino acid occupying a position; and "insertion" means adding one or several amino acids adjacent to an amino acid occupying a position.

The term "MHC", the major histocompatibility complex, refers to a multi-gene locus responsible for the production of histocompatibility antigens. This locus expresses as different symbols for different organisms and as HLA for humans.

The term "HLA antigen" is a histocompatibility antigen and is an antigen determined by the human leukocyte A locus (i.e., the major histocompatibility locus). They are the polypeptides or glycoproteins found in most nucleated cells and platelets, which determine the type of tissue transplanted and are associated with certain diseases.

The term "class I HLA antigen" refers to an antigen encoded by the HLA locus of the human MHC complex.

The term "HLA-A antigen" or "HLA-A" refers to a polymorphism class I human histocompatibility surface antigen present in almost all nucleated cells. They are target antigens for T cell lysis reactions and are also involved in the acceptance or rejection of tissue/organ transplants.

The term "vaccine" refers to a formulation for prevention, diagnosis and treatment prepared from microorganisms or toxins thereof, enzymes, serum or cells of human or animals. In the context of the present application, "vaccine" refers to a formulation that induces an immune response or anti-tumor immunity when inoculated into a subject.

The term "high expression" or "high expression level" as used herein refers to expressing at a higher expression level than in normal tissues.

The term "adherent culture" refers to the culture in which cells are attached to a solid surface. Adherent culture systems mainly include rotary bottles, hollow fibers, glass beads, microcarrier systems and the like.

"T2 cell" refers to a cell line deficient in the antigenic polypeptide transporter (TAP) essential for endogenous pathway of antigen presentation, which is an HLA-A2 positive T and B lymphocyte hybridoma cell, and T2 cell expresses HLA-A0201. It can be used to study the binding of polypeptides to MHC and the mutual recognition of T cells and MHC-molecules.

Polypeptide

The polypeptide of the present invention is derived from tumor's mutated protein, in particular a mutated TWIST Neighbor protein. The asparagine (Asn, N) at position 136 of the amino acid sequence of the mutated TWIST Neighbor protein has been mutated to tyrosine (Tyr, Y), which mutated protein is present in tumor tissues and is expressed at high levels in tumor tissues. Because it exists only in the patient's tumor tissues and not in normal tissues, its specificity is high and the specificity of immune response induced by it is also high. It can be prepared as a peptide vaccine, which is safer, has less side effects, and rarely causes serious immune response in comparison with other tumor polypeptide vaccines, and because its structure is simple and it is easy to synthesize it, it can be developed as a vaccine to induce an immune response against tumors.

The present invention provides a polypeptide or a derivative thereof selected from the group consisting of
- a) a polypeptide comprising or consisting of the amino acid sequence KLMGIVYKV (SEQ ID NO: 2); or
- b) a polypeptide having an amino acid sequence at least 70%, at least 75%, at least 80%, at least 85%, at least 90%, at least 95%, at least 99% identical to SEQ ID NO: 2, wherein said polypeptide has the ability of inducing cytotoxic T lymphocyte cells; or
- c) a polypeptide having an amino acid sequence comprising at least one or several amino acid substitutions, deletions and/or additions compared to SEQ ID NO: 2, wherein said polypeptide has the ability of inducing cytotoxic T lymphocyte cells; or
- d) a polypeptide derivative which is a derivative of any of a)-c), wherein the polypeptide derivative has the ability of inducing cytotoxic T lymphocyte cells.

In a specific embodiment, the present invention provides a polypeptide consisting of 9 amino acids having a molecular weight of 1050.37 Daltons and a full-length sequence of: KLMGIVYKV (SEQ ID NO: 2). The inventors predicted by computer prediction software that the polypeptide sequence has high affinity for HLA-A0201 (also referred to as "HLA-A*0201"). it is confirmed by T2 affinity test that the polypeptide does have a high affinity for HLA-A0201.

The present invention also relates to variants of the polypeptide. The variant comprises amino acid changes at one or more (several) positions, i.e., substitution, insertion and/or deletion of one or more (several) amino acid residues, but still has the activity of the polypeptide, that is, it has high affinity for HLA-A0201 and has CTL-inducing ability. In a particular embodiment, "several" means 5 or less, more preferably 3 or less, and most preferably 2 or less. For example, a variant of the polypeptide may have a substitution, insertion and/or deletion of 5, 4, 3, 2 or 1 amino acid residue compared to the polypeptide set forth in SEQ ID NO:2.

Preferably, the change in amino acid is a conservative substitution. Examples of conservative substitutions are within the following groups: basic amino acid group (arginine, lysine and histidine), acidic amino acid group (glutamic acid and aspartic acid), polar amino acid group (glutamine and asparagine), hydrophobic amino acid group (leucine, isoleucine and valine), aromatic amino acid group (phenylalanine, tryptophan and tyrosine) and small amino acid group (glycine, alanine, serine, threonine and methionine).

In addition to the 20 standard amino acids, non-standard amino acids (e.g., 4-hydroxyproline, 6-N-methyllysine, 2-aminoisobutyric acid, isovaline, and alpha-methylserine) can be used to substitute for amino acid residues in the polypeptide. A limited number of non-conservative amino acids, amino acids not encoded by the genetic code, and non-natural amino acids can be substituted for amino acid residues. Non-natural amino acids can be synthesized by chemical methods, and are preferably commercially available, including, for example, hexahydropyridinecarboxylic acid, thiazolidinecarboxylic acid, dehydroproline, 3- and 4-methylproline, and 3,3-dimethylproline.

Furthermore, essential amino acids in the parent polypeptide can be identified according to methods known in the art, such as site-directed mutagenesis or alanine partition mutagenesis (Cunningham and Wells, 1989, Science 244: 1081-1085). In the latter technique, a single alanine mutation is introduced into each residue in the molecule, and the biological activity of the resulting mutant molecule is tested to identify amino acid residues that are critical to the activity of the molecule. See Hilton et al., 1996, J. Biol. Chem. 271: 4699-4708.

In a preferred embodiment, the polypeptide, wherein the second amino acid from the N-terminus of SEQ ID NO: 2 is substituted with leucine or methionine, and/or the C-terminal amino acid is substituted with proline or leucine, may be used.

In a specific embodiment, the variants of the polypeptide comprises KMMGIVYKV (SEQ ID NO: 3, i.e., the second amino acid from the N-terminus of SEQ ID NO: 2 is substituted with methionine), KLMGIVYKL (SEQ ID NO: 4, i.e., the C-terminal amino acid of SEQ ID NO: 2 is substituted with leucine), KMMGIVYKL (SEQ ID NO: 5, i.e., the second amino acid from the N-terminus of SEQ ID NO: 2 is substituted with methionine, and the C-terminal amino acid is substituted with leucine). The above variants have enhanced affinity for HLA-A0201 without altering their specificity for T cells. Thus, the above variants also have the ability to activate specific T cell immunity. The polypeptide represented by KLMGIVYKV (SEQ ID NO: 2) or a variant thereof can be used as a target or vaccine for the biological treatment of a tumor which expresses both HLA-A0201 and the polypeptide or a variant thereof.

The polypeptide of the present invention can be produced using well-known techniques. For example, the polypeptide can be prepared using recombinant DNA techniques or by methods of chemical synthesis. The polypeptides of the present invention may also be expressed by using viral vectors or bacterial vectors. Examples of suitable expression vectors include, but not limited to, viral vectors such as lentivirus, vaccinia virus, fowlpox virus, adenovirus and adeno-associated virus vectors, retroviral vectors; BCG (Bacille Calmette Guerin) vectors; bacterial vectors, such as *Salmonella typhi* vectors. Preferably, the viral vectors are vectors that have no replication ability and pathogenicity. In a specific embodiment of the present invention, viral vectors are lentiviral vectors.

The polypeptide of the present invention is preferably an isolated polypeptide. The term "isolated polypeptide" as used herein refers to a polypeptide isolated from its source. For example, the polypeptide is at least 60% pure, preferably at least 80% pure, more preferably at least 90% pure, and most preferably at least 95% pure, as determined by SDS-PAGE and HPLC. Preferably, the "isolated polypeptide" is a substantially pure polypeptide. "Substantially pure polypeptide" as used herein refers to a polypeptide preparation which comprises by weight up to 10%, preferably up to 8%, more preferably up to 6%, more preferably up to 5%, more preferably up to 4%, more preferably up to 3%, even more preferably up to 2%, most preferably up to 1%, and even most preferably up to 0.5% of other polypeptide materials to which the polypeptide naturally or recombinantly bind.

The present invention also relates to derivatives of polypeptides. For example, the polypeptide of the present invention may contain modifications, such as glycosylation, side-chain oxidation or phosphorylation modification, as long as the modification does not affect the biological activity of the peptide, i.e., the ability to bind to the HLA antigen and induce CTL. Examples of derivatives of polypeptides also include polypeptides with radiolabels, biotin labels or fluorescent labels. Furthermore, the present invention also encompasses hydrates, solvates, or physiologically acceptable salts of the polypeptides.

Furthermore, the present invention also relates to polynucleotides encoding said polypeptides. The polynucleotides can be designed and prepared based on polypeptide sequences according to methods well known to those skilled in the art.

In a further embodiment, the present invention relates to a nucleic acid construct comprising the polynucleotide of the present invention, and one or more regulatory sequences operably linked thereto that direct expression of the polypeptide in a host cell. Examples of such regulatory sequences include, but not limited to, promoters, enhancers, and the like.

In a further embodiment, the polynucleotides of the present invention can be constructed into vectors, such as viral vectors, bacterial vectors, eukaryotic vectors, and BCG vectors. Examples of viral vectors include, but not limited to, lentivirus, vaccinia virus, fowlpox virus, adenovirus and adeno-associated virus vectors, retroviral vectors, preferably lentiviral vectors. More preferably, the viral vectors are vectors that are attenuated or detoxified. Examples of bacterial vectors include, but not limited to, *Salmonella typhi* vectors, *Bacillus subtilis* vectors, *E. coli* vectors, and the like. Examples of eukaryotic vectors include, but not limited to, yeast vectors, such as *Saccharomyces cerevisiae* vectors.

In a still further embodiment, a nucleic acid construct or vector of the present invention can be transformed or transfected into a host cell. A suitable host cell can be any host cell suitable for expression of the nucleic acid construct or vector. In a specific embodiment, the host cell is a dendritic cell.

Antigen Presenting Cells and Production of Immune Effector Cells

The present invention also relates to an in vitro method of producing antigen presenting cells, the method comprising the steps of:
  (a) contacting an antigen presenting cell with the polypeptide of the present invention or a derivative thereof, or
  (b) introducing a polynucleotide, a nucleic acid construct, or a vector of the present invention into an antigen presenting cell.

In one embodiment, the antigen presenting cells can be induced by inducing dendritic cells from peripheral blood mononuclear cells and contacting the polypeptide of the present invention or a derivative thereof with the dendritic cell in vitro, ex vivo or in vivo, such that the dendritic cells are loaded with the polypeptide or derivative thereof.

The present invention also relates to antigen presenting cells produced by the above methods. The antigen presenting cell presents the polypeptide of the present invention or a derivative thereof on the cell surface. In a specific embodiment, the antigen presenting cell is a dendritic cell loaded with the polypeptide of the present invention.

Further, the present invention relates to a method of producing an immune effector cell, wherein the method comprises the step of contacting the polypeptide of the present invention or a derivative thereof with an immune cell. Specifically, the immune effector cells can be produced by co-cultivating the polypeptide of the present invention or a derivative thereof with a lymphocyte. In one embodiment, the immune cell is a T lymphocyte, preferably a CD8+ T lymphocyte. Specifically, CD8+ T lymphocytes from a subject can be activated as polypeptide-specific CD8+ T lymphocytes upon co-culture of the CD8+ T lymphocytes with dendritic cells loaded with the polypeptide of the present invention.

The present invention also relates to an immune effector cell produced by the above method. Whether the polypeptide of the present invention activates the cellular immune response induced by CD8+ T lymphocytes or not can be verified by the ELISPOTs method, and the killing activity of CD8+ T lymphocytes can be further verified by an LDH release assay.

ELISPOTs (Enzyme Linked ImmunoSpot assays), a commonly used assay in the field of immunology, which combines cell culture techniques with enzyme-linked immunosorbent assays, can detect cytokine secretion at single cell level. The general principle of this method consists in capturing the cytokines secreted by the cells in culture with an antibody and presenting them by means of enzyme-linked spots. The method has high sensitivity and is easy to operate.

The principle of the LDH release assay (i.e., lactate dehydrogenase release assay, also known as LDH release assay or LDH cytotoxicity assay) is that LDH is abundant in the cytosol and cannot pass through cell membrane under normal conditions, however, when the cells are damaged or dead, LDH can be released to the outside of the cell, so that the number of dead cells is directly proportional to the LDH activity in the cell culture medium. LDH in the test well is determined by colorimetry and compared with that in control well of target cells to calculate the cell killing ratio of the effector cell to the target cell. This assay method operates very simple and rapidly, and can be applied to the measurement of cell activity of CTL.

Vaccine

It has been verified by in vitro immunogenicity experiments (ELISPOTs) that the polypeptide of the present invention can induce antigen-specific T cells to secrete IFN-γ cytokines, causing activation of immune cells. Furthermore, LDH release experiments has confirmed that activated CD8+ T cells can specifically recognize target cells presenting the test polypeptide and kill the target cells.

Therefore, the polypeptide of the present invention can be prepared as a vaccine for diagnosis, prevention and treatment of tumors. The vaccine can be in the form of polypeptide+adjuvant, polypeptide-loaded DC vaccine, or polypeptide-specific DC-CTL, DC-CIK vaccine or the like. As known to those skilled in the art, anti-tumor immunity includes, but not limited to, the following immune responses: induction of cytotoxic T lymphocytes; production of antibodies; production of anti-tumor cytokines. When the polypeptide induces any of these immune responses upon inoculation into a subject, the polypeptide can be considered to have an effect of inducing anti-tumor immunity.

Methods for detecting the induction of cytotoxic T lymphocytes are well known in the art. Foreign substances entering the living body are presented to the T cells by antigen presenting cells (APC). T cells that respond to antigens presented by APC in an antigen-specific manner differentiate into cytotoxic T lymphocytes (also called cytotoxic T cells or CTLs) due to the stimulation of the antigen and are amplified. Thus, CTL induction by a polypeptide can be assessed by presenting the polypeptide from APC to T cells and detecting the induction of CTL. Furthermore, APC has the effect of activating CD4+ T cells, CD8+ T cells, and the activation of these cells can be used as an indicator to evaluate the effective induction of anti-tumor immunity of the polypeptide.

Furthermore, methods for evaluating CTL induction using dendritic cells (DC) as APC are well known in the art. In this method, the test polypeptide is first contacted with DC and the DC is then contacted with T cells. T cells having an antigen-specific killing effect are detected after contact with DC, indicating that the test polypeptide has an activity of inducing cytotoxic T lymphocytes. As is known to those skilled in the art, LDH (lactose dehydrogenase) release can be used as an indicator to assess the damage to antigen presenting cells loaded with tumor antigens. Furthermore, it can also be detected by measuring IFN-γ produced and released by CTL in the presence of an antigen presenting cell carrying an immobilized peptide by visualizing IFN-γ with an anti-IFN-γ antibody, such as the ELISPOTs assay used in the present application.

It has been confirmed by these methods that the test polypeptide has CTL-inducing activity, and thus can be used as a vaccine against a disease (e.g., cancer) associated with high expression or mutation of the TWIST Neighbor gene. Further, APC having CTL-inducing activity due to contact with the polypeptide and CTL having cytotoxicity due to presentation of the polypeptide antigen by APC can also be used as vaccines against diseases (for example, cancer) associated with high expression or mutation of the TWIST Neighbor gene. The cancer includes, but not limited to, breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumor.

In one aspect of the present invention, the polypeptide of the present invention may be used in combination with an adjuvant. Examples of suitable adjuvants include, but not limited to, aluminum hydroxide, flu adjuvant, CpG, cholera toxin, *salmonella* toxin, and the like. Additionally, the vaccine of the present invention may optionally be combined with a pharmaceutically acceptable carrier. Examples of such carriers include, but not limited to, sterile water, physiological saline, phosphate buffers, and the like. The vaccine may also contain stabilizers, surfactants, and the like, if desired.

In other embodiments, the vaccine of the present invention may also be in the form comprising the polynucleotide, nucleic acid construct, vector, host cell, antigen presenting cell, targeting immune cell population, or immune effector cell of the present invention.

As known to those skilled in the art, the vaccine can be administered systemically or topically. The vaccine can be administered by single-dose administration or by multi-dose administration, such as prime-boost administration.

When APC or CTL is used as the vaccine of the present invention, a disease (e.g., cancer) associated with high expression or mutation of the TWIST Neighbor gene can be treated or prevented in, for example, an ex vivo manner. Specifically, PBMC of a subject to be treated or prevented may be collected, contacted with a peptide of the present invention in vitro; and administered to a subject after induction of APC or CTL. The in vitro induced APC or CTL can be expanded prior to administration to more effectively treat or prevent the disease. APC can also be induced by introducing a vector encoding the peptide into the PBMC ex vivo.

Antibody

The present invention also relates to an antibody that is capable of specifically recognizing the vaccine of the present invention. The antibodies of the present invention include, but not limited to, polyclonal antibodies, monoclonal antibodies, chimeric antibodies, humanized and primatized antibodies, CDR-grafted antibodies, human antibodies, recombinant antibodies, intracellular antibodies, multi-specific antibodies, bispecific antibodies, monovalent antibodies, multivalent antibodies, immunospecific antibody fragments (such as Fd, Fab, F(ab')2, F(ab') fragments), single-stranded fragments (e.g., ScFv and ScFvFc); and their derivatives. The antibodies of the present invention can comprise all classes of antibodies (i.e., IgA, IgD, IgE, IgG, and IgM) and all subclasses (i.e., IgG1, IgG2, IgG3, IgG4, IgA1, and IgA2).

The antibodies of the present invention can be produced using a variety of methods known in the art. For example, polyclonal antibodies can be produced in a host animal; monoclonal antibodies can be produced by hybridoma technology, recombinant techniques, phage display technology, transgenic animals, and the like. In a specific embodiment, the serum of an animal immunized with the vaccine of the present invention is collected, and the antibody of interest is purified from the serum to prepare the antibody of the present invention.

Once the antibody of the present invention is produced, it can be further modified to provide an antibody having improved activity. For example, the antibody can be modified or altered by molecular biology techniques to provide derivatized antibodies that provide the desired therapeutic properties. The derived antibodies include, but not limited to, chimeric antibodies, humanized antibodies, and the like.

The antibodies of the present invention may also be conjugated, linked or otherwise fused or otherwise associated to other active ingredients, such as anti-cancer drugs. Suitable anti-cancer drugs include, but not limited to, abarelix, aclarubicin, aminopurine, aldesleukin, alemtuzumab, asteady, altretamine, amifostine, aminoglutethimide, anakinra, anastrozole, azacitidine, bleomycin, bortezomib, busulfan, capecitabine, carboplatin, carmustine, cetuximab, chlorambucil, cisplatin, cladribine, clofarabine, cyclophosphamide, cytarabine, dacarbazine, dasatinib, decitabine, docetaxel, exemestane, gemtuzumab, Rituximab, vincristine, vindesine, vorinostat, zoledronic acid. Furthermore, the antibodies of the present invention can be conjugated to a biocompatible modifying agent to modulate, alter, improve or adjust antibody characteristics. For example, an antibody or fusion construct having increased in vivo half-life can be produced by combining with polymer molecules having a relatively high molecular weight, such as commercially available polyethylene glycols, i.e., PEG, or similar biocompatible polymers.

The antibody of the present invention can be used for the treatment and prevention of diseases associated with high expression of the TWISTNB gene or mutation(s) in the TWISTNB gene, such as cancer. The cancer includes, but not limited to, breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumor.

A person skilled in the art can formulate an antibody into a suitable dosage form as needed, and appropriately adjust the dose of the antibody depending on the disease to be treated, the age, body weight of the subject, the administration method, and the like.

Pharmaceutical Composition

The polypeptide of the present invention can be formulated as a pharmaceutical composition for administration to a subject. In the pharmaceutical composition, in addition to the polypeptide of the present invention, a pharmaceutically acceptable carrier, excipient, adjuvant, or the like can be included. Exemplary adjuvants include, but not limited to, aluminum phosphate, aluminum hydroxide, and alum. Furthermore, the pharmaceutical composition can comprise other active ingredients, such as anti-cancer drugs. Suitable anti-cancer drugs include, but not limited to, abarelix, aclarubicin, aminopurine, aldesleukin, alemtuzumab, asteady, altretamine, amifostine, aminoglutethimide, anakinra, anastrozole, azacitidine, bleomycin, bortezomib, busulfan, capecitabine, carboplatin, carmustine, cetuximab, chlorambucil, cisplatin, cladribine, clofarabine, cyclophosphamide, cytarabine, dacarbazine, dasatinib, decitabine, docetaxel, exemestane, gemtuzumab, Rituximab, vincristine, vindesine, vorinostat, zoledronic acid.

Furthermore, the pharmaceutical composition of the present invention can also be in the form comprising the polynucleotide, nucleic acid construct, vector, host cell, antigen presenting cell, targeting immune cell population or immune effector cell of the present invention. A person skilled in the art can formulate the pharmaceutical compositions into suitable dosage forms, such as liposomes, granules, powders, and the like, as desired. The composition can be administered systemically or topically to a target tumor by, for example, oral, intradermal, subcutaneous route, or intravenous injection, and the like.

A person skilled in the art can appropriately adjust the dosage of the polypeptide in the pharmaceutical composition of the present invention depending on the disease to be treated, the age, weight of the subject, the method of administration, and the like, as the selection and optimization of these dosages is within the capabilities of the person skilled in the art. The dose of the polypeptide is usually from 0.001 mg to 1000 mg, preferably from 0.01 mg to 100 mg, more preferably from 0.1 mg to 10 mg, for example 3 mg.

The pharmaceutical composition can be used for the treatment and prevention of diseases associated with high expression of the TWISTNB gene or mutation(s) in the TWISTNB gene, such as cancer. The cancer includes, but not limited to, breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumor.

Kit

The present invention also relates to a kit comprising the polypeptide or derivative thereof, the polynucleotide, the nucleic acid construct, the vector, the host cell, the antigen presenting cell, the targeting immune cell population, the immune effector cell, the vaccine, or the antibody of the present invention in one or more containers, and optionally, instructions for using the kit. Suitable containers include, for example, vials, syringes, and the like. The containers may be formed from a variety of materials such as glass or plastic.

In certain embodiments, the kit further contains one or more additional agents and, optionally, one or more anti-cancer agents. Suitable anti-cancer drugs include, but not limited to, abarelix, aclarubicin, aminopurine, aldesleukin, alemtuzumab, asteady, altretamine, amifostine, aminoglutethimide, anakinra, anastrozole, azacitidine, bleomycin, bortezomib, busulfan, capecitabine, carboplatin, carmustine, cetuximab, chlorambucil, cisplatin, cladribine, clofarabine, cyclophosphamide, cytarabine, dacarbazine, dasatinib, decitabine, docetaxel, exemestane, gemtuzumab, Rituximab, vincristine, vindesine, vorinostat, zoledronic acid.

When the components of the kit are provided in one or more liquid solutions, the liquid solution can be a non-aqueous or aqueous solution, preferably a sterile aqueous solution. The formulation in the kit can also be provided as a dry powder or in a lyophilized form which may be reconstituted after the addition of a suitable liquid. The liquid used for reconstitution can be contained in separate containers. Such liquid can contain sterile pharmaceutically acceptable buffers or other diluents such as bacteriostatic water for injection, phosphate buffered saline, Ringer's solution or dextrose solution.

Application of the Present Invention

The Twist neighbor protein encoded by the TWISTNB gene functions as a DNA-dependent RNA polymerase in normal organisms, and as a component of RNA polymerase I, it catalyzes DNA to RNA transcription and is lowly expressed in normal tissues of adults. However, the mutated TWISTNB gene is capable of expressing at high levels in tumor tissues.

The present inventors have surprisingly found that the polypeptide of the present invention can induce specific T cells to secrete IFN-γ, causing activation of immune cells, and it has been confirmed by LDH release experiments that CD8+ T cells can specifically recognize the target cells presenting the polypeptide of the present invention and kill the target cells.

Thus, the polypeptide of the present invention can be used to: produce antigen presenting cells capable of inducing cytotoxic T cell; and induce cytotoxic T lymphocytes.

In particular, the application of the present invention lies in at least the following aspects.

A. Diagnosis or Detection of Diseases

The present invention can be used to diagnose or detect diseases associated with high expression of the TWISTNB gene or mutation(s) in the TWISTNB gene.

In one aspect, the diseases associated with high expression of the TWISTNB gene or mutation(s) in the TWISTNB gene in a subject can be diagnosed by obtaining serum from the subject and detecting the presence of the polypeptide of the present invention or derivative thereof in the serum.

In another aspect, the antibody of the present invention can also be used to detect or diagnose diseases associated with high expression of the TWISTNB gene or mutation(s) in the TWISTNB gene in a subject. Optionally, the antibody can be conjugated to a diagnostic agent, a detectable agent, a label or a reporter (e.g., a biomolecule, a small molecule compound, a fluorophore, or a radioisotope).

In one embodiment, the disease associated with high expression of the TWISTNB gene or mutation(s) in the TWISTNB gene is cancer, including breast cancer, lung cancer, nasopharyngeal carcinoma, liver cancer, gastric cancer, esophageal cancer, colorectal cancer, pancreatic cancer, melanin Tumor, skin cancer, prostate cancer, cervical cancer, leukemia, brain tumors. In a specific embodiment, the cancer is lung cancer, particularly non-small cell lung cancer, more particularly non-small cell line lung adenocarcinoma.

In one embodiment, the subject is a mammal, preferably a human, a non-human primate, a mouse, a rat, a dog, a cat, a horse or a cow. In a specific embodiment, the subject is a human.

In one embodiment, the subject's HLA antigen is an HLA-A2 subtype, preferably an HLA-A0201 subtype.

B. Prevention or Treatment of Diseases

The present invention can be used for the prevention or treatment of diseases associated with high expression of the TWISTNB gene or mutation(s) in the TWISTNB gene.

Specifically, the polypeptide or derivative thereof, the polynucleotide, the nucleic acid construct, the vector, the host cell, the antigen presenting cell, the targeting immune cell population, the immune effector cell, the vaccine, or the antibody of the present invention can be used for prevention or treatment of diseases associated with high expression of the TWISTNB gene or mutation(s) in the TWISTNB gene in a subject, and can also be used for the manufacture of a medicament for preventing or treating diseases associated with high expression of the TWISTNB gene or mutation(s) in the TWISTNB gene in a subject. In a preferred embodiment, the disease associated with high expression of the TWISTNB gene or mutation(s) in the TWISTNB gene is cancer. Specifically, the cancer includes breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, brain tumor. Preferably, the cancer is cervical cancer, colorectal cancer, colorectal cancer, pancreatic cancer, gastric cancer.

The subject is a mammal, preferably a human, a non-human primate, a mouse, a rat, a dog, a cat, a horse or a cow. In a specific embodiment, the subject is a human.

The subject's HLA antigen is an HLA-A2 subtype, preferably an HLA-A0201 subtype.

A person skilled in the art can formulate the drug into a suitable dosage form such as a liposome, a granule, a powder, and the like, as desired. The composition can be administered systemically or topically to a target tumor by, for example, oral, intradermal, subcutaneous route, or intravenous injection, and the like.

A person skilled in the art can appropriately adjust the dosage of the polypeptide or derivative thereof, the polynucleotide, the nucleic acid construct, the vector, the host cell, the antigen presenting cell, the targeting immune cell population, the immune effector cell, the vaccine, or the antibody in the medicament of the present invention based on the disease to be prevented or treated, the age, body weight of the subject, the administration method, and the like, as the selection and optimization of these dosages is within the capabilities of the person skilled in the art.

In the following examples, various aspects of the present invention will be described. The examples are intended for purposes of illustration only and are not intended to limit the scope of the present invention in any way.

Example

Example 1. Synthesis and Purification of the Polypeptides

The polypeptides of the present invention were synthesized according to standard solid phase synthesis methods and purified by reverse phase HPLC. The purity (>90%) and identity of the polypeptides were determined by HPLC and mass spectrometry, respectively.

Example 2. Affinity Prediction of the Polypeptides for HLA-A0201

Based on the selected HLA (HLA-A0201 in the specific embodiment of the present invention) allelic typing, our self-developed software "Software for binding predictions of mutated polypeptides on the basis of tumor DNA and RNA sequencing" (Chinese Software Copyright No.: 2016SR002835) was used to predict the affinity of the polypeptides. The predicted results were expressed as IC50, and the lower the IC50, the higher the affinity of the polypeptide for HLA allele typing. In particular, an IC50 of less than 500 indicates that the polypeptide has affinity for HLA-A0201, and an IC50 of less than 50 indicates that the polypeptide has high affinity for HLA-A0201.

Affinity predictions were performed on the mutated polypeptides (SEQ ID NOs: 2-5) and the wild-type polypeptide (SEQ ID NO: 6), and the mutated polypeptides having an IC50 of less than 500 and less than that of the wild-type polypeptide were screened for the next T2 affinity verification.

The predicted affinity scores of the mutated polypeptides (SEQ ID NOs: 2-5) and the wild type polypeptide for HLA-A0201 are shown in Table 1.

TABLE 1

| Mutated polypeptide sequence | IC50 (nM) | Wild type polypeptide sequence | IC50 (nM) |
|---|---|---|---|
| KLMGIVYKV (SEQ ID NO: 2) | 2.88 | KLMGIVNKV (SEQ ID NO: 6) | 3.63 |
| KMMGIVYKV (SEQ ID NO: 3) | 2.68 | — | — |
| KLMGIVYKL (SEQ ID NO: 4) | 2.36 | — | — |
| KMMGIVYKL (SEQ ID NO: 5) | 2.47 | — | — |

It can be seen that the mutated polypeptidse of SEQ ID NOs: 2-5 of the present invention were predicted to have high affinity for HLA-A0201, and their affinity for HLA-A0201 is higher than that of the wild-type polypeptide sequence for HLA-A0201. Therefore, the polypeptides of the present invention (SEQ ID NOs: 2-5) were selected to further verify their affinity for HLA-A0201.

Example 3. Affinity Verification of the Polypeptides for HLA-A0201

$2*10^5$ T2 cells (American Type Culture Collection (ATCC); CRL-1992™) were resuspended in 500 ul of IMDM serum-free medium (Cat. No. 12440-053, GIBCO) containing human β2 microglobulin (final concentration, 3 ug/ml) in a 24-well plate, and the polypeptides of SEQ ID NOs: 2-5 of the present invention and the wild-type polypeptide (final concentration of 100 μM, respectively) were added and incubated in an incubator (37 C, 5% $CO_2$) overnight. 2 duplicate wells per group were used. T2 cells to which no polypeptide was added were used as a background control, and T2 cells to which CMV (NLVPMVATV) polypeptide was added were used as a positive control. The cells were collected by centrifugation at 200 g for 5 minutes. After the collected cells were washed twice with PBS (Cat. No. 10010-031, GIBCO), the cells were directly incubated with anti-HLA-A 0201 FITC monoclonal antibody and incubated at 4 C for 30 minutes. The mean fluorescence intensity (MFI) was then detected and analyzed by flow cytometry (BD FACSJazz™) and its software, as shown in FIG. 1.

The fluorescence index (FI) is calculated using the following formula:

$$FI=[\text{Mean Fluorescence Intensity (MFI)}_{sample}-MFI_{background}]/MFI_{background},$$

wherein the $MFI_{background}$ represents the value without the polypeptide.

FI>1.5 indicates that the polypeptide has high affinity for HLA-A 0201 molecule, 1.0<FI<1.5 indicates that the polypeptide has moderate affinity for HLA-A 0201 molecule, and 0.5<FI<1.0 indicates that the polypeptide has low affinity for HLA-A 0201 molecule.

The affinities of the polypeptides of the present invention for T2 cells as determined by flow cytometry are shown in Table 2.

TABLE 2

Affinity detection of the polypeptides for HLA-A0201

| Sample | Concentration of the added polypeptide | MFI | FI |
|---|---|---|---|
| KLMGIVNKV (SEQ ID NO: 6) (wild type) | 100 μM | 647.8 | 1.89 |
| KLMGIVYKV (SEQ ID NO: 2) | 100 μM | 665.7 | 1.97 |
| KMMGIVYKV (SEQ ID NO: 3) | 100 μM | 681.6 | 2.04 |
| KLMGIVYKL (SEQ ID NO: 4) | 100 μM | 723.6 | 2.23 |
| KMMGIVYKL (SEQ ID NO: 5) | 100 μM | 692.3 | 2.09 |
| Blank | 100 μM | 223.7 | 0 |
| CMV | 100 μM | 681.6 | 2.04 |

For the polypeptides of the present invention (SEQ ID NOs: 2-5), FI is greater than 1.5, further demonstrating that the polypeptides of the present invention have high affinity for HLA-A0201.

Example 4. Cell Expansion of CD8+ T Cells Stimulated by the Polypeptides In Vitro Dendritic cells (DCs) derived from monocytes were used as antigen presenting cells (APCs) to induce CTL responses against peptides presented on HLA. $2 \times 10^8$ peripheral blood mononuclear cells (PBMC) were isolated from 100 ml of peripheral blood of healthy volunteers with positive HLA-A0201 subtype using Ficoll lymphocyte separation solution (Cat. No. 17-1440-02, GE Healthcare). Mononuclear cells were obtained by adherent culture (3 hours), and CD8+ T cells in PBMC cells were screened with CD8 magnetic beads. GM-CSF (1000 U/ml) and IL-4 (1000 U/ml) were used to induce adherent monocytes into immature DCs, then IFN-γ (100 U/ml), LPS (10 ng/ml), and the polypeptides of the present invention as set forth in SEQ ID NOs: 2-5 were used to induce adherent cells into mature DC cells. The mature DC cells loaded with the polypeptides were irradiated (dose of 25 Gy) and co-cultured with CD8+ T cells of the volunteers (DC density was $5 \times 10^5$ cells/ml, CD8+ T cell density was $2 \times 10^6$ cells/ml, both of DCs and CD8+ T cells were mixed in equal volume and added to the well plate, i.e., co-cultured) with IL-21 added, then IL-2 and IL-7 were replenished after 3 days, and then IL-2 and IL-7 were replenished once on day 5 and 7, respectively. Co-cultured cells (co-cultured CD8+ T cells were activated to polypeptide-specific CD8+ T cells) were counted on day 10. The cell counts are shown in Table 3:

TABLE 3

Cell counts after culture

| | Total number of cells in the well before culture | Total number of cells in the well after culture |
|---|---|---|
| KLMGIVYKV (SEQ ID NO: 2) | $2.5 \times 10^6$ | $1.32 \times 10^7$ |
| KMMGIVYKV (SEQ ID NO: 3) | $2.5 \times 10^6$ | $1.37 \times 10^7$ |
| KLMGIVYKL (SEQ ID NO: 4) | $2.5 \times 10^6$ | $1.63 \times 10^7$ |
| KMMGIVYKL (SEQ ID NO: 5) | $2.5 \times 10^6$ | $1.46 \times 10^7$ |

The above results indicate that the polypeptides of the present invention significantly stimulate the expansion of CD8+ T cells. After 10 days of culture, the cells proliferated significantly, and the total number of cells expanded by 5-7 times.

Example 5. Verification of the Activation of CD8+ T Cell Immune Response by the Polypeptides by Using Enzyme-Linked Immunospot Assays (ELISPOTs) Method The principle of ELISPOTs detection method is that CD8+ T cells can specifically recognize the complex of HLA-A0201 and a polypeptide, and with different polypeptide sequence, the T cell population recognizing the complex of HLA-A0201 and the polypeptide is also different. As T2 cells express HLA-A0201, CD8+ T cells can specifically recognize T2 cells loaded with mutated polypeptides, but cannot recognize T2 cells loaded with wild-type polypeptide. After specifically recognizing the complex of HLA-A0201 and the polypeptide, the polypeptide-specific CD8+ T cells are able to reactivate and secrete IFN-γ. The IFN-γ secreted by activation of CD8+ T cells is captured by a biotin-labeled secondary antibody. It is then bound to alkaline phosphatase or peroxide horseradish oxidase-labeled streptavidin. Spots are formed by the color development of the substrate. The number of spots represents the number of cells that are activated to secrete IFN-γ.

The cells co-cultured in Example 4 and T2 cells loaded with the mutated polypeptides or the wild-type polypeptide were added into human IFN-γ ELISPOTs plates for culture and detection. The spots formed by the ELISPOT test were finally counted. The requirement for the test polypeptide to be immunogenic is as follows: the number of spots (test polypeptide)/the number of spots (wild type polypeptide)>2, that is, the number of spots formed by the test polypeptide is more than twice the number of spots formed by the wild type polypeptide.

The cells co-cultured in Example 4 and T2 cells loaded with the mutated polypeptide KLMGIVYKV (SEQ ID NO: 2) and its variable formats (SEQ ID NOs: 2-5) and the wild type polypeptide KLMGIVNKV (SEQ ID NO: 6) were added into human IFN-γ ELISPOTs plates for culture, and subjected to ELISPOTs test (Mabtech, Cat. No. 3420-4APW-2) 20 hours later.

Figure 2:
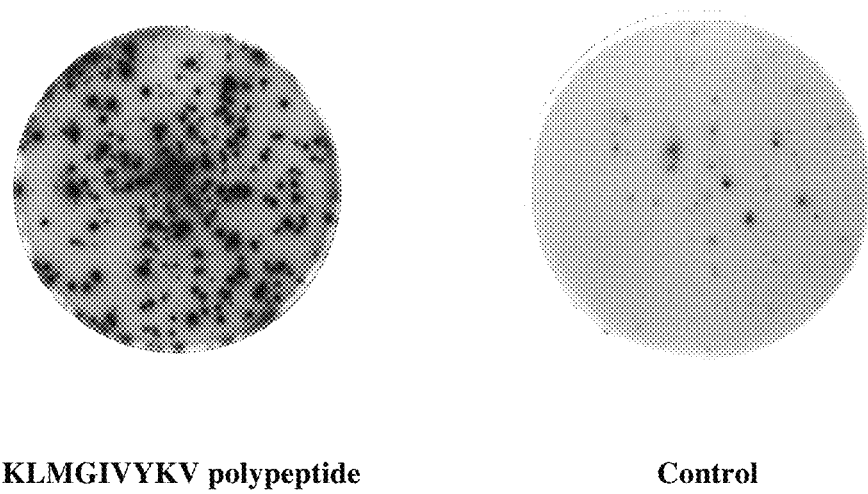
FIG. 2 shows that the KLMGIVYKV polypeptide (SEQ ID NO: 2) of the present invention activates the CD8+ T cell immune response by the enzyme-linked immunospot assays (ELISPOTs) method. Co-cultured CD8+ T cells and T2 cells respectively loaded with KLMGIVYKV polypeptide (SEQ ID NO: 2) and wild-type polypeptide were added to ELISPOTs plates, and after 20 hours of culture, ELISPOTs detection were performed. The left panel shows the number of spots for cells loaded with the KLMGIVYKV polypeptide (SEQ ID NO: 2), and the right panel shows the number of spots for cells loaded with the wild-type polypeptide ("Control"). The sequence shown in FIG. 2 is SEQ ID NO: 2.

The results of ELISPOTs are shown in FIG. 2 and Table 4.

TABLE 4

Polypeptides stimulated specific CD8+ T cells to secrete IFN-γ interferon

| Polypeptide sequence with which DCs were loaded | Number of spots in the mutated polypeptide group | Number of spots in the wild type polypeptide group | Folds (test/wild type) | Conclusion |
| --- | --- | --- | --- | --- |
| KLMGIVYKV (SEQ ID NO: 2) | 316 | 31 | 10.01 | immunogenic |
| KMMGIVYKV (SEQ ID NO: 3) | 323 | 37 | 8.73 | immunogenic |
| KLMGIVYKL (SEQ ID NO: 4) | 335 | 40 | 8.34 | immunogenic |
| KMMGIVYKL (SEQ ID NO: 5) | 328 | 29 | 11.31 | immunogenic |

The number of spots formed by the mutated polypeptides is much higher (more than twice) than the number of spots formed by the wild type polypeptide, indicating that the mutated polypeptides are strongly immunogenic.

Example 6. LDH Release Assay Demonstrates the Specific Killing Activity of CD8+ T Cell by Polypeptides The following experiment was carried out according to the instructions of Pierce™ LDH Cytotoxicity Assay Kit (Thermo, Cat. No. 88953). The co-cultured cells in Example 4 were co-cultured with T2 cells loaded with mutated polypeptides or wild-type polypeptide or T2 cells without any loaded polypeptides. In the experiment, the maximum release well, the volume correction well, the medium control well, the spontaneous release well, the control of different ratios of effective cells to target cells (the ratio of the number of T cells to the T2 cell) and the like were set, and three duplicate wells were set in each group, and after 4 hours, 50 ul of the supernatant of the co-cultured cells was collected and added to 50 ul of LDH substrate mixture to catalyze the reaction of LDH substrate. After 30 minutes, 50 ul of reaction stop solution was added and read the 490 nm wavelength and the reference wavelength of 680 nm, and the killing activity of target cells against T2 cells were calculated based on the control wells.

The formula for calculating the killing activity is:

Killing efficiency (%)=(test well–spontaneous release of effector cell–spontaneous release of target cell+medium well)/(maximum release of target cell–volume correction well–spontaneous release of target cell+medium well)×100%

Figure 3:
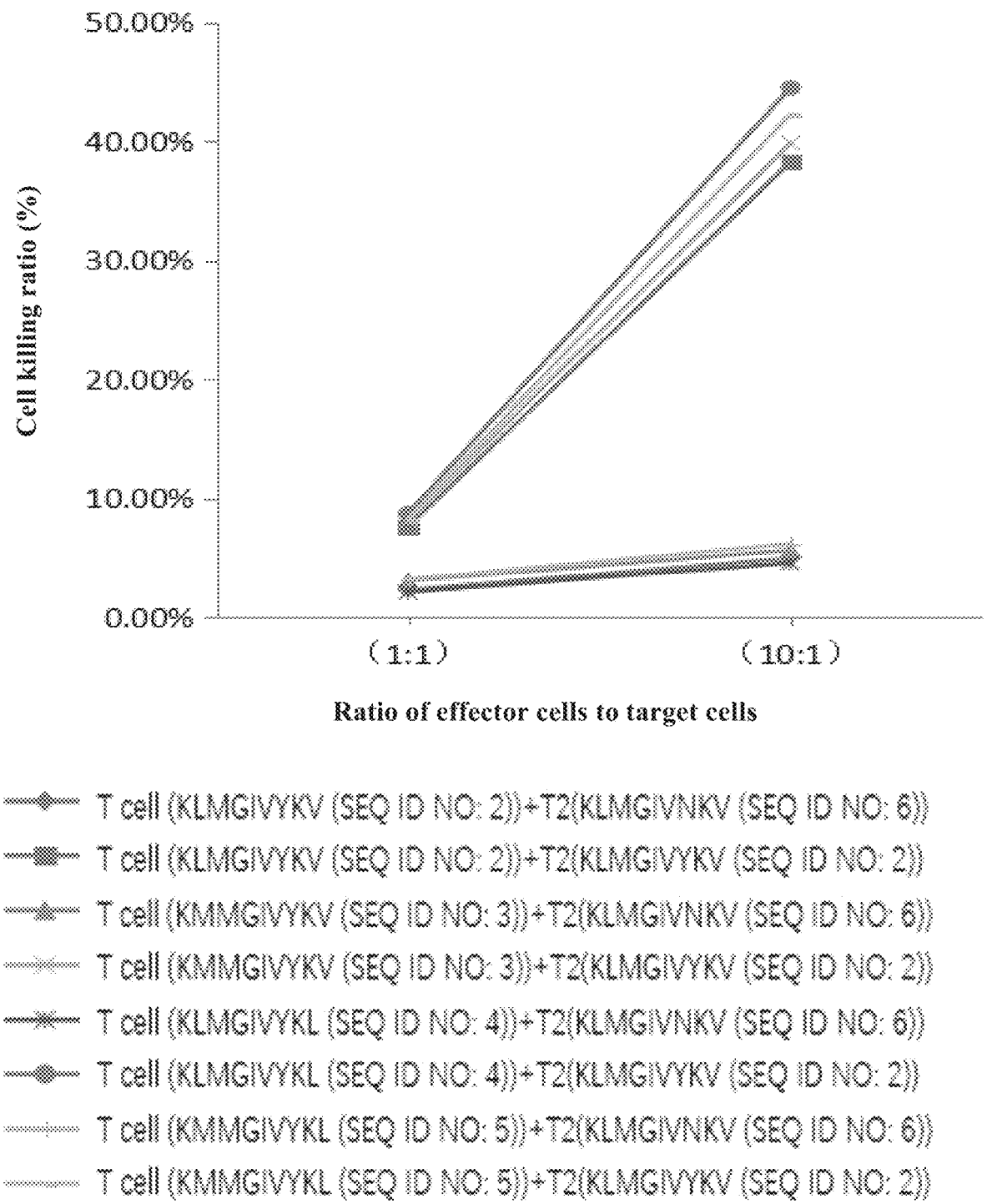
FIG. 3 shows the cell killing ratio (%) of CD8+ T cells for specifically killing target cells presenting mutated polypeptides, wild-type polypeptides, and not loaded with polypeptides.

The results of the killing efficiency are shown in FIG. 3 and Table 5.

TABLE 5

T cells specifically recognize and kill target cells that present test polypeptides

| Group | Ratio of effective cells to target cells (1:1) | Ratio of effective cells to target cells (10:1) |
| --- | --- | --- |
| T cell (KLMGIVYKV (SEQ ID NO: 2)) + T2 (KLMGIVNKV (SEQ ID NO: 6)) | 2.33% | 5.03% |
| T cell (KLMGIVYKV (SEQ ID NO: 2)) + T2 (KLMGIVYKV (SEQ ID NO: 2)) | 7.69% | 38.29% |
| T cell (KMMGIVYKV (SEQ ID NO: 3)) + T2 (KLMGIVNKV (SEQ ID NO: 6)) | 3.12% | 5.71% |
| T cell (KMMGIVYKV (SEQ ID NO: 3)) + T2 (KLMGIVYKV (SEQ ID NO: 2)) | 8.18% | 39.86% |
| T cell (KLMGIVYKL (SEQ ID NO: 4)) + T2 (KLMGIVNKV (SEQ ID NO: 6)) | 2.17% | 4.63% |
| T cell (KLMGIVYKL (SEQ ID NO: 4)) + T2 (KLMGIVYKV (SEQ ID NO: 2)) | 8.76% | 44.52% |
| T cell (KMMGIVYKL (SEQ ID NO: 5)) + T2 (KLMGIVNKV (SEQ ID NO: 6)) | 3.25% | 6.23% |
| T cell (KMMGIVYKL (SEQ ID NO: 5)) + T2 (KLMGIVYKV (SEQ ID NO: 2)) | 8.29% | 42.26% |

The above results indicate that when the ratio of effective cells to target cells is 1:1 or 1:10, the T cells activated by mutated polypeptides can kill the T2 cells that present the mutated polypeptides, but not the T2 cells that present the wild-type polypeptide, which further confirms that the mutated polypeptides are capable of specifically killing target cells that present the mutated polypeptides. Especially when the ratio of effective cells to target cells is 1:10, the killing efficiency of T cells against T2 cells loaded with mutated polypeptides is significantly higher than that of T cells against T2 cells loaded with wild-type polypeptide, and it is also significantly higher than that of T cells against T2 cells without any loaded polypeptides. Thus, it can be seen that CD8+ T cells are capable of killing target cells carrying the mutated polypeptides of the present invention with high specificity.

Example 7. Construction and Packaging of Recombinant Lentiviruses with Wild-Type Polypeptide or Mutated Polypeptides Using automated DNA synthesizer, nucleotide sequences were synthesized by ligating nucleotides one by one based on a known sequence utilizing solid phase phosphite amide method. The following sequences were synthesized: the DNA sequence corresponding to the wild type KLM- GIVNKV (SEQ ID NO: 6) polypeptide "AAGCT-TATGGGTATAGTTAATAAAGTG" (SEQ ID NO: 7), the polynucleotide sequence corresponding to the mutated polypeptide KLMGIVYKV (SEQ ID NO: 2) "AAGCT-TATGGGTATAGTTTATAAAGTG" (SEQ ID NO: 8), the polynucleotide sequence corresponding to the mutated polypeptide KMMGIVYKV (SEQ ID NO: 3) "AAGAT-GATGGGTATAGTTTATAAAGTG" (SEQ ID NO: 9), the polynucleotide sequence corresponding to the mutated polypeptide KLMGIVYKL (SEQ ID NO: 4) "AAGCT-TATGGGTATAGTTTATAAACTG" (SEQ ID NO: 10) and the corresponding polypeptide sequence of the mutated polypeptide KMMGIVYKL (SEQ ID NO: 5) "AAGAT-GATGGGTATAGTTTATAAACTG" (SEQ ID NO: 11). The lentiviral plasmids pHBLV-Puro containing the wild type polypeptide or the mutated polypeptides were separately constructed and named as pHBLV-Puro-KLMGIVNKV, pHBLV-Puro-KLMGIVYKV, pHBLV-Puro-KMMGIVYKV, pHBLV-Puro-KLMGIVYKL, pHBLV-Puro-KMMGIVYKL, respectively. Thereafter, the five lentiviral plasmids were co-transfected into T293 cells with the pSPAX2 and pMD2G helper plasmids, respectively, and were packaged into lentiviruses containing the wild type polypeptide or the mutated polypeptides.

Example 8. Establishment of a Subcutaneous Xenograft Model of H2087-KLMGIVYKV (SEQ ID NO: 2)

8.1 Establishment of a Human-Derived Lung Cancer Cell Line Expressing KLMGIVYKV (SEQ ID NO: 2) Polypeptide Human lung (non-small cell) adenocarcinoma cell line NCI-H2087 was purchased from ATCC, and its HLA subtype is HLA-A0201 positive (Rao M, et al. Inhibition of histone lysine methylation enhances cancer-testis antigen expression in lung cancer cells: implications for adoptive immunotherapy of cancer. Cancer research. 2011; 71:4192-204). The cells were cultured in DMEM medium supplemented with 10% fetal calf serum, 100 U/mL penicillin and streptomycin in an incubator at 37° C., 5% $CO_2$. The packaged KLMGIVYKV (SEQ ID NO: 2) lentivirus was transfected into the H2087 cell line, and the surviving H2087 cell line was continuously screened with Puromycin antibiotic, and finally the H2087 cell line expressing the KLMGIVYKV (SEQ ID NO: 2) polypeptide was established and designated as the H2087-KLMGIVYKV (SEQ ID NO: 2) cell line.

8.2 Human Immune Reconstitution of NOD SCID Mice 300-600 ml of anticoagulated peripheral blood were collected from healthy volunteers. Peripheral blood mononuclear cells (PBMC) were isolated by Ficoll and the cells were collected for further use. A total of 300 NOD SCID mice excluding immune leakage were each intraperitoneally injected with $2 \times 10^7$ PBMC per 0.5 ml for human immune reconstitution. Mice after 4 weeks were selected to be inoculated with the human-derived lung cancer cell line as established in Section 8.1 above.

8.3 Construction of Human Non-Small Cell Line Lung Adenocarcinoma Tumor Model

The established human lung (non-small cell) adenocarcinoma cell line H2087-KLMGIVYKV cells were cultured in DMEM medium supplemented with 10% fetal calf serum, 100 U/mL penicillin and streptomycin in an incubator at 37° C., 5% $CO_2$. H2087-KLMGIVYKV tumor cells (cultured overnight in fresh medium) were collected, centrifuged at 1500 rpm for 5 minutes, and washed 3 times with sterile physiological saline. After appropriate dilution, 40 μl of the cell suspension was stained with 10 μl of 0.4% Trypan Blue and microscopically counted to prepare a tumor cell suspension at a concentration of $1 \times 10^8$ cells/ml. NOD/SCID mice or NOD/SCID mice subjected to immunological reconstruction were selected for subcutaneously inoculation with 100 ul of the tumor cell suspension per mouse. After the inoculation was completed, whether the inoculation site is infected or not and whether there is natural regression after tumor growth or not were observed day by day. Using the vernier caliper, the tumor long diameter a and the short diameter b were measured every 2-3 days, and the tumor size was calculated as follows: tumor size=a*b*b/2. After 7 days, the subcutaneous tumor of the mice can be touched as a tumor of about the size of a rice grain, and then the NOD/SCID mice of the H2087-KLMGIVYKV (SEQ ID NO: 2) subcutaneous tumor model were treated with DC-CTL vaccine. The NOD/SCID mice of H2087-KLMGIVYKV (SEQ ID NO: 2) subcutaneous tumor model subjected to immunological reconstitution for 4 weeks were treated with polypeptide+complete Freund's adjuvant, or polypeptide+DC vaccine, or lentivirus-infected DC cell vaccine, and the tumor volume and the survival rate of the mice were recorded every 2 days.

Example 9. Treatment Regimen Using Polypeptide Vaccine

Figure 4:
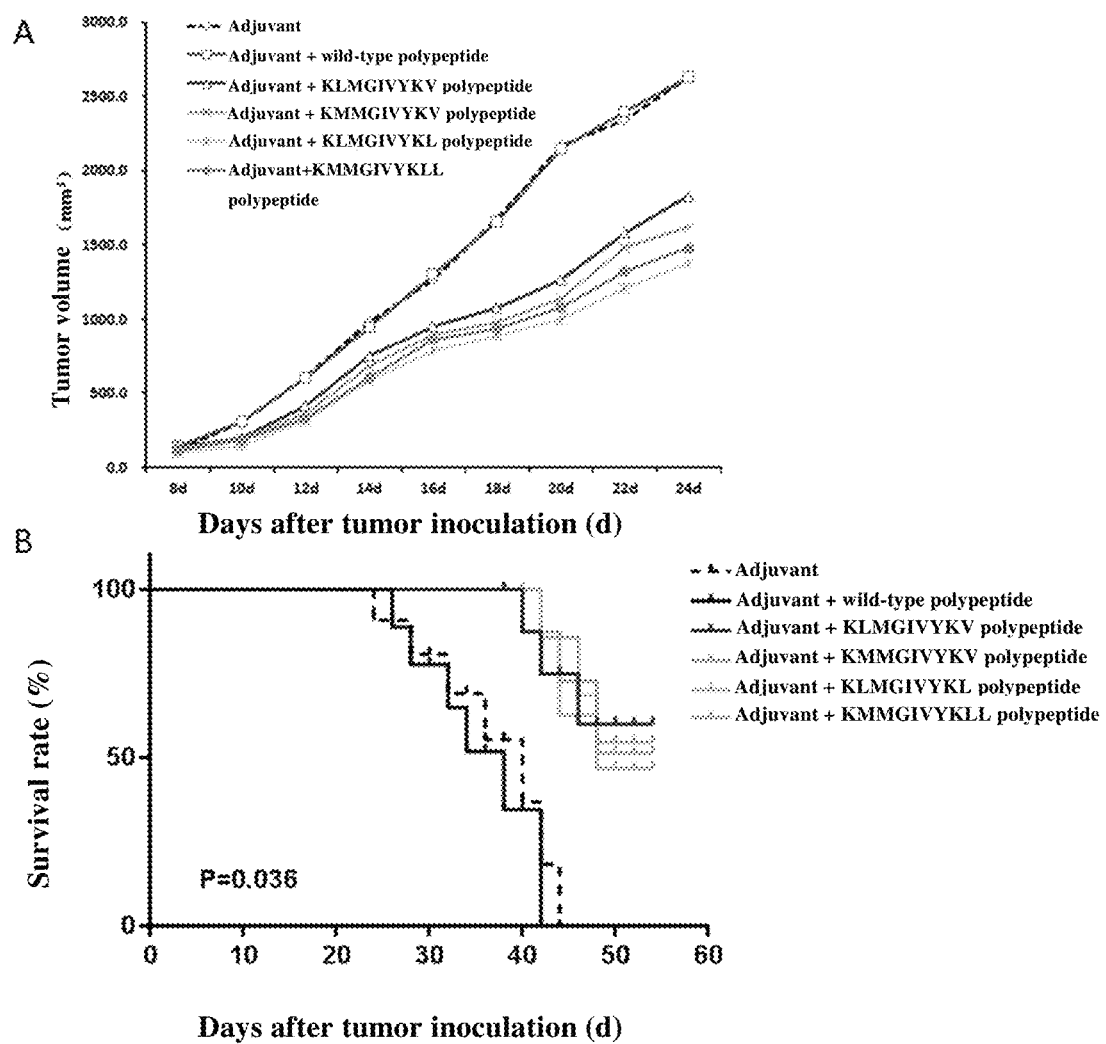
FIG. 4 shows the inhibitory effect of immunotherapy using mutated polypeptide on tumor growth and the survival rate after treatment.

Tumor-bearing mice were randomly divided into 6 groups: adjuvant, adjuvant+wild type polypeptide, adjuvant+KLMGIVYKV (SEQ ID NO: 2) polypeptide, adjuvant+KMMGIVYKV (SEQ ID NO: 3) polypeptide, adjuvant+KLMGIVYKL (SEQ ID NO: 4) polypeptide, and adjuvant+KMMGIVYKL (SEQ ID NO: 5) polypeptide, with 6 mice in each group. The first immunization dose of the polypeptides was 100 ug/mouse. The polypeptides were resuspended in PBS, mixed with 150 ul Freund's complete adjuvant per mouse, adjusted to 300 ul/mouse with PBS, and injected subcutaneously at two sites on the back. After 2 weeks, the same dose was used for booster immunization for 4 times (complete Freund's adjuvant was used for the first time, and incomplete Freund's adjuvant was used for the other 3 times). The general characteristics of the tumor-bearing mice were observed daily, including mental status, activity, response, diet, body weight, tumor growth, and the like. The longest diameter (a) and the shortest diameter (b) of the tumor were measured with a vernier caliper every 2 days. The tumor volume was calculated as: ½×length×width². The results are shown in FIG. 4.

The results showed that the mutated polypeptides (SEQ ID NOs: 2-5, respectively)+Freund's adjuvant were effective in both inhibiting tumor growth and prolonging the survival of the mice, compared to the adjuvant alone and the wild type polypeptide.

Survival rate is calculated according to the following formula:

Survival rate within a certain period of time=survived mice within this certain period of time/(survived mice within this certain period of time+dead mice within this certain period of time)*100%.

Example 10. Treatment Regimen Using DC Polypeptide Vaccine 10.1 Preparation of DC Polypeptide Vaccine 100 to 150 ml of anticoagulated peripheral blood were collected from healthy volunteers. Peripheral blood mononuclear cells (PBMC) were isolated by Ficoll. PBMC cells were harvested, resuspended in RPMI 1640 medium at 2 to $3 \times 10^6$/ml, and incubated at 37° C. for 2 hours. The adherent cells were DC. The non-adherent cells were collected as peripheral blood lymphocytes (PBL) for further use. The adherent cells were induced into mature DC cells using 1000 U/ml GM-CSF, 1000 U/ml IL-4, 100 U/ml, IFN-gamma, 10 ng/ml LPS. After harvesting the mature DCs, the mutated polypeptides (SEQ ID NOs: 2-5, final concentration of 10 pg/ml) were added, and after 4 hours of incubation, the mature DCs were washed 3 times with physiological saline. The DCs loaded with the polypeptides were adjusted to $(4.0 \pm 0.5) \times 10^7$ cells/ml with physiological saline for subsequent experiments.

Figure 5:
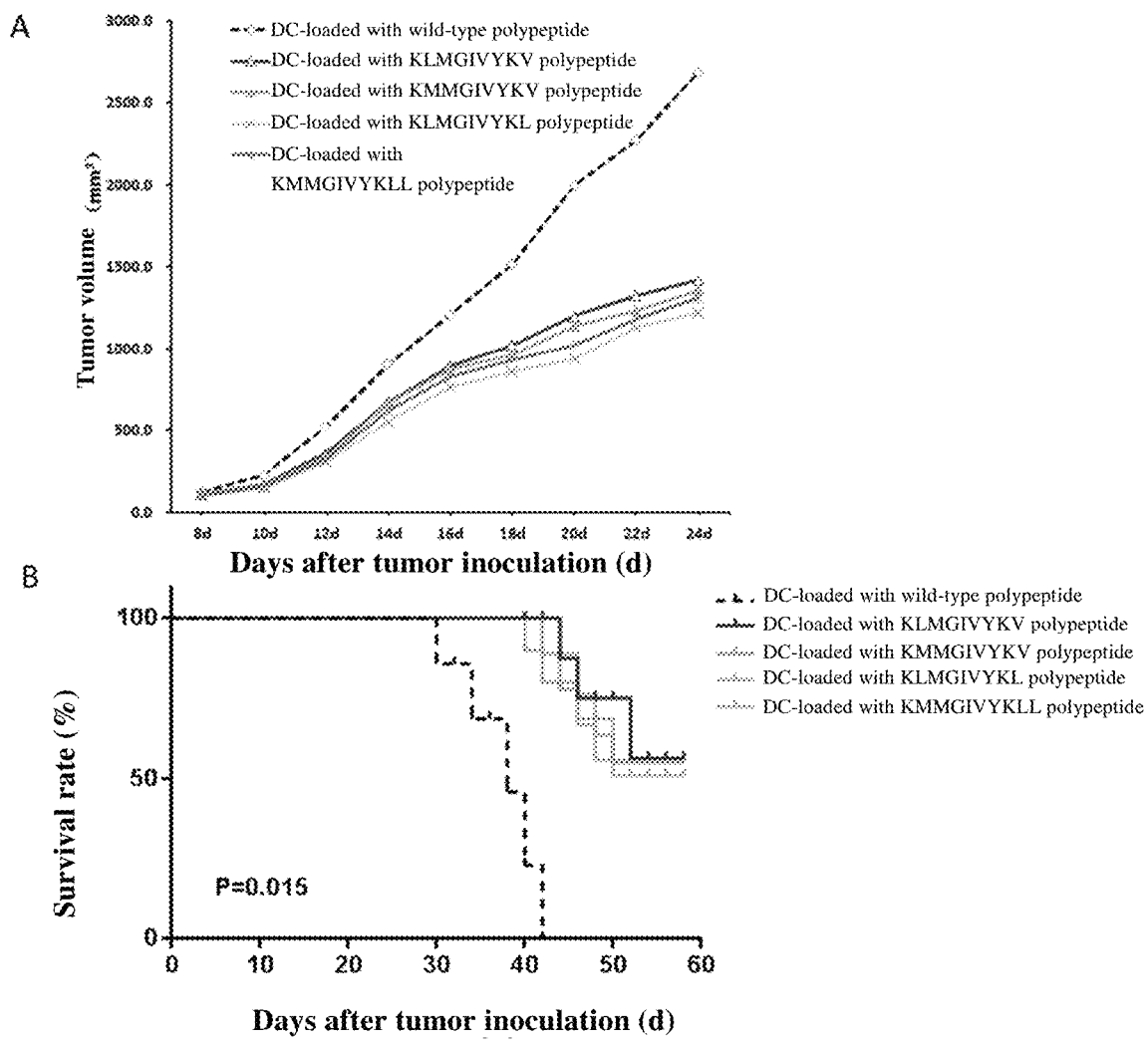
FIG. 5 shows the inhibitory effect of immunotherapy using DC-mutated polypeptide on tumor growth and the survival rate after treatment.

10.2 Effect of Polypeptide-Loaded DC Vaccine on Survival and Tumor Growth in Mice Tumor-bearing mice were randomly divided into 5 groups: DC-loaded with wild-type polypeptide, DC-loaded with KLMGIVYKV (SEQ ID NO: 2) polypeptide, DC-loaded with KMMGIVYKV (SEQ ID NO: 3) polypeptide, DC-loaded with KLMGIVYKL (SEQ ID NO: 4) polypeptide, and DC-loaded with KMMGIVYKL (SEQ ID NO: 5) polypeptide, with 6 mice in each group. Cell suspension of the DC-loaded with KLMGIVYKV (SEQ ID NO: 2) polypeptide, DC-loaded with KMMGIVYKV (SEQ ID NO: 3) polypeptide, DC-loaded with KLMGIVYKL (SEQ ID NO: 4) polypeptide, and DC-loaded with KMMGIVYKL (SEQ ID NO: 5) polypeptide were prepared ($4 \times 10^7$ cells/ml). The tumor-bearing mice were intradermally injected at the inner thigh of the inguinal region, with 0.1 ml at each side for once a week. The dose was $(4.0 \pm 0.5) \times 10^6$ cells/time, with a total of 2 times of injections. After injections, the vital signs of the mice were observed, and the vertical and horizontal dimensions of the tumor were measured with vernier calipers every 2 days (Klebanoff C A, Finkelstein S E, Surman D R, Lichtman M K, Gattinoni L, Theoret M R, et al. IL-15 enhances the in vivo antitumor activity of tumor-reactive CD8+ T cells. Proceedings of the National Academy of Sciences of the United States of America. 2004; 101:1969-74). Tumor volume was calculated as: tumor volume=½×length×width$^2$. The changes in body weight and the survival of the mice were simultaneously recorded. The results are shown in FIG. 5.

The results showed that the DC vaccine group loaded with the mutated polypeptides (SEQ ID NOs: 2-5) significantly prolonged the survival of the mice and slowed down the tumor growth of the mice relative to the DC vaccine group loaded with the wild-type polypeptide (SEQ ID NO: 6).

Example 11. Treatment Regimen Using Nucleic Acid Transfected DC Vaccine 11.1 Preparation of Nucleic Acid Transfected DC Vaccine 100 to 150 ml of anticoagulated peripheral blood were collected from healthy volunteers. Peripheral blood mononuclear cells (PBMC) were isolated by Ficoll. PBMC cells were harvested and incubated at 37° C. for 2 hours, non-adherent cells were washed away, and recombinant human granulocyte-macrophage colony-stimulating factor (rhGM-CSF), recombinant human interlukin-4 (rhIL-4) were used to culture DC cells. On the fifth day of culture, half of the DC culture medium was replaced and the cell density was adjusted to $1 \times 10^6$ cells/ml; lentivirus culture medium (containing 50 ul of lentivirus culture medium per 1 ml DC culture medium) that expresses the wild type polypeptide and the mutated polypeptides (SEQ ID NOs: 2-5) was added. After 24 hours, the virus culture medium was removed, and a culture medium containing 50 ng/ml rhIL-4, 100 ng/ml rh GM-CSF, 100 U/ml IFN-γ and 10 ng/ml LPS was added and placed in an incubator at 37° C. 5% $CO_2$ for culture. After 48 to 72 hours, the lentivirus-infected DC cells were observed under a fluorescence microscope, and mature DC cells were collected for treatment of a mouse tumor model.

11.2 Treatment Regimen Using Nucleic Acid Transfected DC Vaccine

Figure 6:
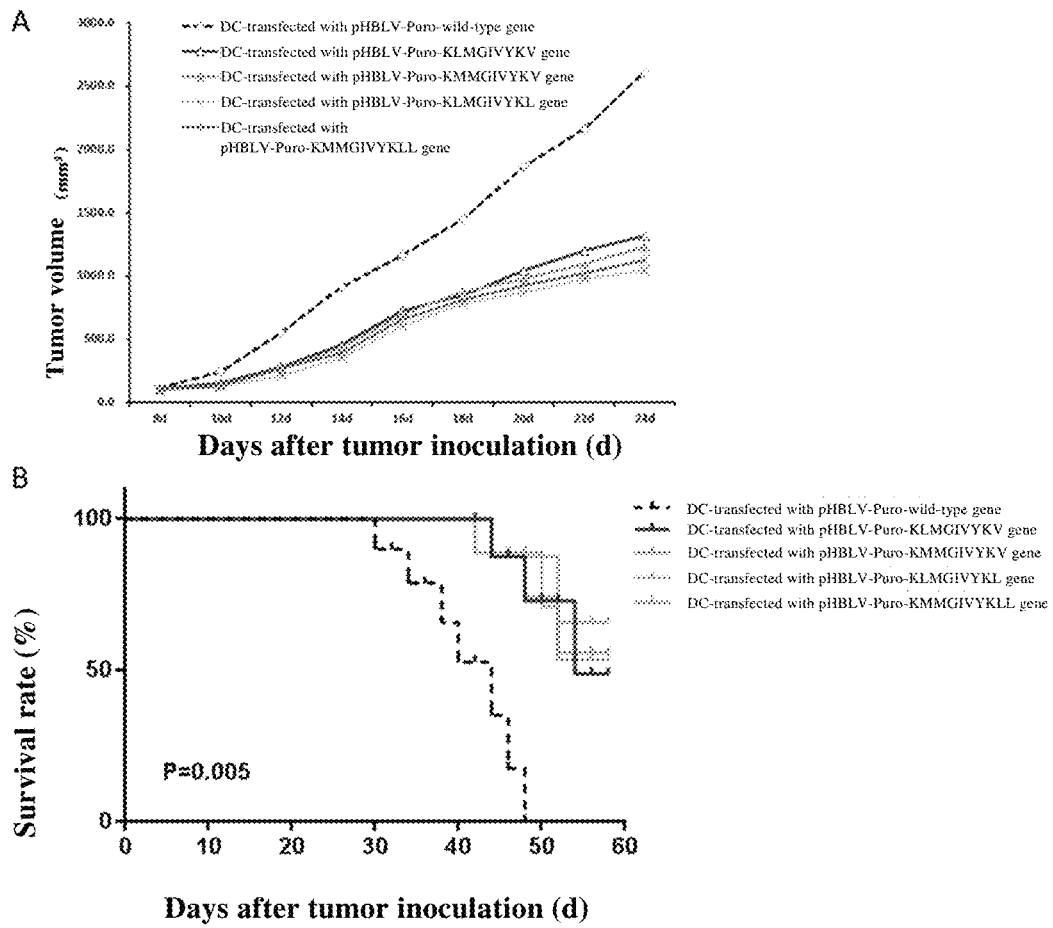
FIG. 6 shows the inhibitory effect of immunotherapy using lentiviral carrying polypeptides on tumor growth and the survival rate after treatment.

Tumor-bearing mice were randomly divided into 5 groups: wild-type polypeptide-DC, mutated polypeptides (SEQ ID NOs: 2-5, respectively)-DC, with 6 mice in each group. Cell suspension of DC-loaded with wild-type polypeptide, DC-loaded with mutated polypeptides ($4 \times 10^7$ cells/ml) were prepared. The tumor-bearing mice were intradermally injected at the inner thigh of the inguinal region, with 0.1 ml at each side for once a week. The dose was $(4.0 \pm 0.5) \times 10^6$ cells/time, with a total of 2 times of injections. After injections, the vital signs of the mice were observed, and the vertical and horizontal dimensions of the tumor were measured with vernier calipers every 2 days (Klebanoff C A, Finkelstein S E, Surman D R, Lichtman M K, Gattinoni L, Theoret M R, et al. IL-15 enhances the in vivo antitumor activity of tumor-reactive CD8+ T cells. Proceedings of the National Academy of Sciences of the United States of America. 2004; 101:1969-74). Tumor volume was calculated as: tumor volume=½×length×width 2. The changes in body weight and the survival of the mice were simultaneously recorded. The results are is shown in FIG. 6.

The results showed that compared to the lentivirus of the wild-type polypeptide, the lentiviral-infected DC vaccine of the mutated polypeptides had a significant tumor suppressing effect and prolonged the survival of the mice, whereas the wild-type polypeptide had no effect on the tumor.

Figure 7:
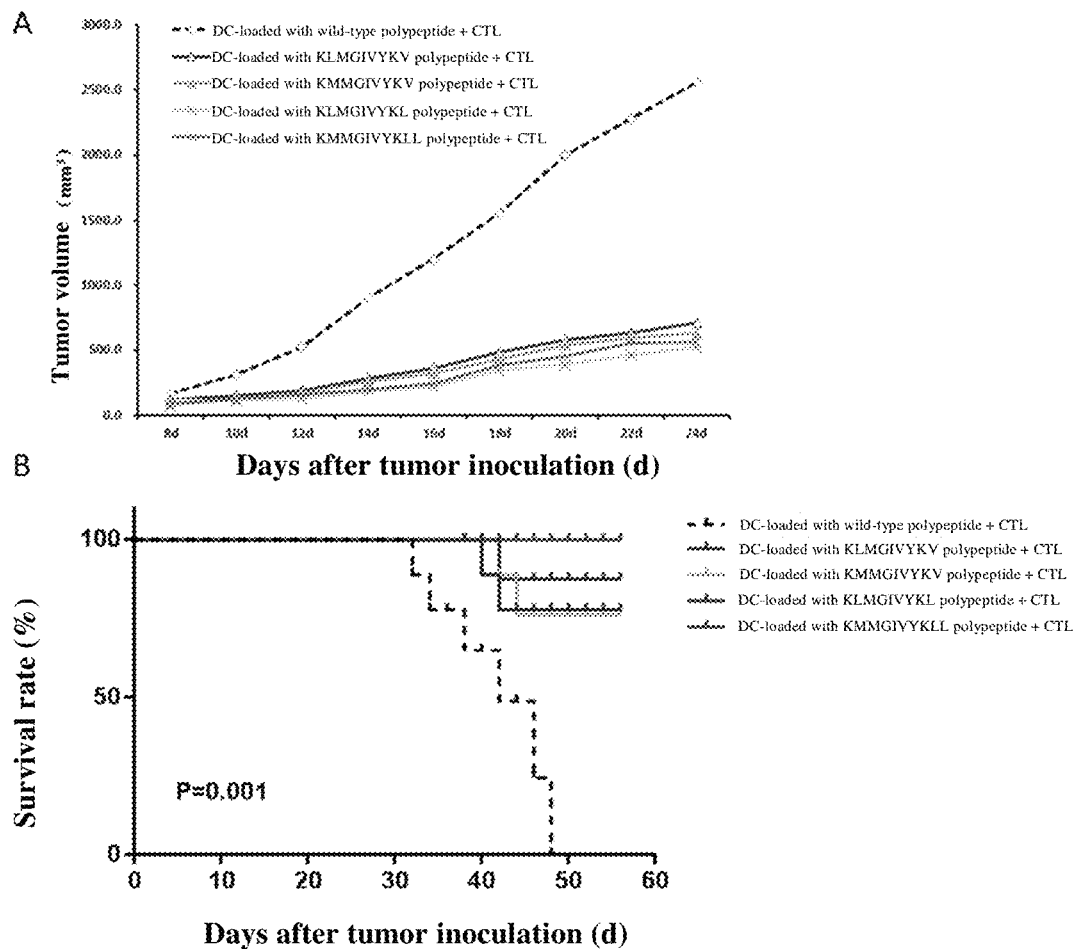
FIG. 7 shows the inhibitory effect of immunotherapy using DC-loaded with polypeptide+CTL on tumor growth and the survival rate after treatment.

Example 12. In vivo DC-CTL treatment regimen 12.1 Preparation of polypeptide-specific CTL vaccine The PBLs collected in Example 10.2 were subjected to magnetic bead sorting to obtain CD8$^+$T, which were incubated with DC loaded with wild-type polypeptide and DC loaded with mutated polypeptides (DC:CD8$^+$T=1:4) for sensitization. 500 IU/ml IL-2 and 50 ng/ml IL-7 were added to the culture medium, and the cells were co-incubated at 37° C. 5% $CO_2$ in an incubator. After 1 week of culture, the cells were counted. At the 2nd week, DCs loaded with the mutated polypeptides, DCs loaded with the wild-type polypeptide were used for a second round of stimulation. Three rounds of co-stimulation were applied, and the appropriate culture medium were added during the culture. The number of lymphocytes was counted on Day 0, 7, 14, and 21, respectively, and the cell proliferation index (PI) was calculated. PI=number of cells after expansion/number of cells inoculated. Cells were harvested after 21 days of culture, i.e., cytotoxic T lymphocytes (CTL). The cells were resuspended in saline ($5 \times 10^8$ cells/ml) in a volume of 0.2 ml and returned to the mice via the tail vein. The number of returned cells per tumor model mouse was about $1 \times 10^8$ cells. After injections, the vital signs of the mice were observed, and the vertical and horizontal dimensions of the tumor were measured with vernier calipers every 2 days (McCormack E, Adams K J, Hassan N J, Kotian A, Lissin N M, Sami M, et al. Bi-specific TCR-anti CD3 redirected T-cell targeting of NY-ESO-1- and LAGE-1-positive tumors. Cancer immunology, immunotherapy: CII. 2013; 62:773-85). The results are shown in FIG. 7.

The results showed that the DC-CTL vaccine activated by the mutated polypeptides (SEQ ID NOs: 2-5) had a remarkable effect of inhibiting tumor growth and prolonged the survival of the mice relative to the wild type polypeptide group.

The above results indicate that the polypeptide of the present invention is highly immunogenic, capable of binding HLA-A0201 antigen with high affinity, has CTL-inducing ability, stimulates expansion of CD8+ T cells, enables CD8+ T cell to specifically kill target cells loaded with the polypeptide of the present invention, slows down tumor growth, and prolongs the survival of the subject. Therefore, the polypeptide of the present invention can be used for the prevention or treatment of diseases in which the TWISTNB gene is expressed at a high level or the TWISTNB gene is mutated.

The present invention has been described in detail by reference to the preferred embodiments of the present invention. However, a person skilled in the art would understand that the above description is only for the purpose of illustration and explanation, and does not aim to limit the scope of the present invention in any way. A person skilled in the art can easily make various changes and modifications to the present invention without departing from the spirit and scope of the present invention. Therefore, the scope of the present invention is defined by the appended claims and their equivalents.

What is claimed is:

1. A method of treatment, comprising:

identifying a subject as having a cancer that has high expression of the TWISTNB gene or mutation(s) in the TWISTNB gene; and administering to the subject an effective amount of a pharmaceutical composition comprising an isolated polypeptide or a polynucleotide encoding said polypeptide, said polypeptide comprising or consisting of the following amino acid sequence:

KLMGIVYKV; (SEQ ID NO: 2)

KMMGIVYKV; (SEQ ID NO: 3)

KLMGIVYKL; (SEQ ID NO: 4)

or

KMMGIVYKL. (SEQ ID NO: 5)

2. The method according to claim 1, wherein the cancer comprises breast cancer, lung cancer, nasopharyngeal cancer, liver cancer, gastric cancer, esophageal cancer, colorectal cancer, pancreatic cancer, melanoma, skin cancer, prostate cancer, cervical cancer, leukemia, or brain tumors.

3. The method according to claim 1, wherein the subject is a mammal.

4. The method according to claim 1, wherein the subject's HLA antigen is an HLA-A2 subtype.

5. The method according to claim 1, wherein the subject is a human.

6. The method according to claim 1, wherein the subject's HLA antigen is an HLA-A0201 subtype.

* * * * *

SEQUENCE LISTING

```
<160> NUMBER OF SEQ ID NOS: 11

<210> SEQ ID NO 1
<211> LENGTH: 338
<212> TYPE: PRT
<213> ORGANISM: Homo sapiens

<400> SEQUENCE: 1

Met Ala Ala Gly Cys Ser Glu Ala Pro Arg Pro Ala Ala Ser Asp
1               5                   10                  15

Gly Ser Leu Val Gly Gln Ala Gly Val Leu Pro Cys Leu Glu Leu Pro
                20                  25                  30

Thr Tyr Ala Ala Ala Cys Ala Leu Val Asn Ser Arg Tyr Ser Cys Leu
            35                  40                  45

Val Ala Gly Pro His Gln Arg His Ile Ala Leu Ser Pro Arg Tyr Leu
        50                  55                  60

Asn Arg Lys Arg Thr Gly Ile Arg Glu Gln Leu Asp Ala Glu Leu Leu
65                  70                  75                  80

Arg Tyr Ser Glu Ser Leu Leu Gly Val Pro Ile Ala Tyr Asp Asn Ile
                85                  90                  95

Lys Val Val Gly Glu Leu Gly Asp Ile Tyr Asp Asp Gln Gly His Ile
                100                 105                 110

His Leu Asn Ile Glu Ala Asp Phe Val Ile Phe Cys Pro Glu Pro Gly
            115                 120                 125

Gln Lys Leu Met Gly Ile Val Asn Lys Val Ser Ser Ser His Ile Gly
        130                 135                 140

Cys Leu Val His Gly Cys Phe Asn Ala Ser Ile Pro Lys Pro Glu Gln
145                 150                 155                 160

Leu Ser Ala Glu Gln Trp Gln Thr Met Glu Ile Asn Met Gly Asp Glu
                165                 170                 175

Leu Glu Phe Glu Val Phe Arg Leu Asp Ser Asp Ala Ala Gly Val Phe
            180                 185                 190

Cys Ile Arg Gly Lys Leu Asn Ile Thr Ser Leu Gln Phe Lys Arg Ser
        195                 200                 205

Glu Val Ser Glu Val Thr Glu Asn Gly Thr Glu Glu Ala Ala Lys
    210                 215                 220

Lys Pro Lys Lys Lys Lys Lys Lys Asp Pro Glu Thr Tyr Glu Val
225                 230                 235                 240

Asp Ser Gly Thr Thr Lys Leu Ala Asp Asp Ala Asp Asp Thr Pro Met
                245                 250                 255
```

```
Glu Glu Ser Ala Leu Gln Asn Thr Asn Asn Ala Asn Gly Ile Trp Glu
            260                 265                 270

Glu Glu Pro Lys Lys Lys Lys Lys Lys His Gln Glu Val Gln
        275                 280                 285

Asp Gln Asp Pro Val Phe Gln Gly Ser Asp Ser Gly Tyr Gln Ser
    290                 295                 300

Asp His Lys Lys Lys Lys Lys Arg Lys His Ser Glu Glu Ala Glu
305                 310                 315                 320

Phe Thr Pro Pro Leu Lys Cys Ser Pro Lys Arg Lys Gly Lys Ser Asn
                325                 330                 335

Phe Leu

<210> SEQ ID NO 2
<211> LENGTH: 9
<212> TYPE: PRT
<213> ORGANISM: Artificial Sequence
<220> FEATURE:
<223> OTHER INFORMATION: synthetic sequence

<400> SEQUENCE: 2

Lys Leu Met Gly Ile Val Tyr Lys Val
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic sequence

<400> SEQUENCE: 3

Lys Met Met Gly Ile Val Tyr Lys Val
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic sequence

<400> SEQUENCE: 4

Lys Leu Met Gly Ile Val Tyr Lys Leu
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic sequence

<400> SEQUENCE: 5

Lys Met Met Gly Ile Val Tyr Lys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic sequence

<400> SEQUENCE: 6
```

```
Lys Leu Met Gly Ile Val Asn Lys Val
1               5

<210> SEQ ID NO 7
<211> LENGTH: 27
<212> TYPE: DNA
<213> ORGANISM: Artificial Sequence
<220> FEATURE:
<223> OTHER INFORMATION: synthetic sequence

<400> SEQUENCE: 7
aagcttatgg gtatagttaa taaagtg                                          27

<210> SEQ ID NO 8
<211> LENGTH: 27
<212> TYPE: DNA
<213> ORGANISM: Artificial Sequence
<220> FEATURE:
<223> OTHER INFORMATION: synthetic sequence

<400> SEQUENCE: 8
aagcttatgg gtatagttta taaagtg                                          27

<210> SEQ ID NO 9
<211> LENGTH: 27
<212> TYPE: DNA
<213> ORGANISM: Artificial Sequence
<220> FEATURE:
<223> OTHER INFORMATION: synthetic sequence

<400> SEQUENCE: 9
aagatgatgg gtatagttta taaagtg                                          27

<210> SEQ ID NO 10
<211> LENGTH: 27
<212> TYPE: DNA
<213> ORGANISM: Artificial Sequence
<220> FEATURE:
<223> OTHER INFORMATION: synthetic sequence

<400> SEQUENCE: 10
aagcttatgg gtatagttta taaactg                                          27

<210> SEQ ID NO 11
<211> LENGTH: 27
<212> TYPE: DNA
<213> ORGANISM: Artificial Sequence
<220> FEATURE:
<223> OTHER INFORMATION: synthetic sequence

<400> SEQUENCE: 11
aagatgatgg gtatagttta taaactg                                          27
```